United States Patent
Cragg et al.

(10) Patent No.: US 7,569,056 B2
(45) Date of Patent: *Aug. 4, 2009

(54) METHODS AND APPARATUS FOR FORMING SHAPED AXIAL BORES THROUGH SPINAL VERTEBRAE

(75) Inventors: Andrew H. Cragg, Edina, MN (US); Jonathan Kagan, Hopkins, MN (US)

(73) Assignee: TranS1 Inc., Wilmington, NC (US)

( * ) Notice: Subject to any disclaimer, the term of this patent is extended or adjusted under 35 U.S.C. 154(b) by 627 days.

This patent is subject to a terminal disclaimer.

(21) Appl. No.: 10/853,476

(22) Filed: May 25, 2004

(65) Prior Publication Data
US 2004/0220577 A1 Nov. 4, 2004

Related U.S. Application Data

(63) Continuation of application No. 09/710,369, filed on Nov. 10, 2000, now Pat. No. 6,740,090.

(60) Provisional application No. 60/182,748, filed on Feb. 16, 2000.

(51) Int. Cl.
*A61B 17/00* (2006.01)
*A61B 17/32* (2006.01)
*A61B 17/56* (2006.01)

(52) U.S. Cl. .......................... 606/79; 606/61; 606/80; 606/180

(58) Field of Classification Search ............ 606/61, 606/79, 80, 96, 113, 159, 170, 180; 408/127; 407/36–38
See application file for complete search history.

(56) References Cited

U.S. PATENT DOCUMENTS 1,630,239 A 5/1927 Binkley et al.

(Continued)

FOREIGN PATENT DOCUMENTS

DE 38 40 466 A1 6/1990

(Continued)

OTHER PUBLICATIONS

J.J. Trambert, MD., "Percutaneous Interventions in the Presacral Space: CT-guided Precoccygeal Apporach—Eary Experience", Radiology 1999; 213: 901-904.

(Continued)

*Primary Examiner*—Julian W Woo
(74) *Attorney, Agent, or Firm*—Knobbe, Martens, Olson & Bear, LLP

(57) ABSTRACT

One or more shaped axial bore extending from an accessed posterior or anterior target point are formed in the cephalad direction through vertebral bodies and intervening discs, if present, in general alignment with a visualized, trans-sacral axial instrumentation/fusion (TASIF) line in a minimally invasive, low trauma, manner. An anterior axial instrumentation/fusion line (AAIFL) or a posterior axial instrumentation/fusion line (PAIFL) that extends from the anterior or posterior target point, respectively, in the cephalad direction following the spinal curvature through one or more vertebral body is visualized by radiographic or fluoroscopic equipment. Preferably, curved anterior or posterior TASIF axial bores are formed in axial or parallel or diverging alignment with the visualized AAIFL or PAIFL, respectively, employing bore forming tools that can be manipulated from proximal portions thereof that are located outside the patient's body to adjust the curvature of the anterior or posterior TASIF axial bores as they are formed in the cephalad direction. Further bore enlarging tools are employed to enlarge one or more selected section of the anterior or posterior TASIF axial bore(s), e.g., the cephalad bore end or a disc space, so as to provide a recess therein that can be employed for various purposes, e.g., to provide anchoring surfaces for spinal implants inserted into the anterior or posterior TASIF axial bore(s).

19 Claims, 24 Drawing Sheets

U.S. PATENT DOCUMENTS

| | | |
|---|---|---|
| 2,336,338 A | 12/1943 | Zublin |
| 3,367,326 A | 2/1968 | Frazier |
| 3,554,192 A | 1/1971 | Isberner |
| 3,892,232 A | 7/1975 | Neufeld |
| 4,135,506 A | 1/1979 | Ulrich |
| 4,170,990 A | 10/1979 | Baumgart et al. |
| 4,175,555 A | 11/1979 | Herbert |
| 4,265,231 A | 5/1981 | Scheller, Jr. et al. |
| 4,401,112 A | 8/1983 | Rezaian |
| 4,453,539 A | 6/1984 | Raftopoulos et al. |
| 4,541,423 A | 9/1985 | Barber |
| 4,553,273 A | 11/1985 | Wu |
| 4,554,914 A | 11/1985 | Kapp et al. |
| 4,573,448 A | 3/1986 | Kambin |
| 4,609,370 A | 9/1986 | Morrison |
| 4,636,217 A | 1/1987 | Ogilvie et al. |
| 4,640,271 A | 2/1987 | Lower |
| 4,650,466 A * | 3/1987 | Luther ................. 606/159 |
| 4,657,550 A | 4/1987 | Daher |
| 4,756,649 A | 7/1988 | Heule |
| 4,844,088 A | 7/1989 | Kambin |
| 4,858,601 A | 8/1989 | Glisson |
| 4,862,891 A | 9/1989 | Smith |
| RE33,258 E | 7/1990 | Onik et al. |
| RE33,348 E | 9/1990 | Lower |
| 4,966,604 A | 10/1990 | Reiss |
| 4,969,888 A | 11/1990 | Scholten et al. |
| 5,002,546 A | 3/1991 | Romano |
| 5,009,659 A * | 4/1991 | Hamlin et al. ............ 606/159 |
| 5,015,255 A | 5/1991 | Kuslich |
| 5,019,079 A | 5/1991 | Ross |
| 5,030,201 A | 7/1991 | Palestrant |
| 5,059,193 A | 10/1991 | Kuslich |
| 5,062,850 A | 11/1991 | MacMillan et al. |
| 5,071,437 A | 12/1991 | Steffee |
| 5,131,382 A | 7/1992 | Meyer |
| 5,147,404 A | 9/1992 | Downey |
| 5,171,279 A | 12/1992 | Mathews |
| 5,190,546 A | 3/1993 | Jervis |
| 5,192,326 A | 3/1993 | Bao et al. |
| 5,195,968 A | 3/1993 | Lundquist et al. |
| 5,236,460 A | 8/1993 | Barber |
| 5,242,443 A | 9/1993 | Kambin |
| 5,242,444 A | 9/1993 | MacMillan |
| 5,242,461 A | 9/1993 | Kortenbach et al. |
| 5,258,031 A | 11/1993 | Salib et al. |
| 5,269,785 A | 12/1993 | Bonutti |
| 5,285,795 A | 2/1994 | Ryan et al. |
| 5,290,289 A | 3/1994 | Sanders et al. |
| 5,313,962 A | 5/1994 | Obenchain |
| 5,336,223 A | 8/1994 | Rogers |
| 5,357,983 A | 10/1994 | Mathews |
| 5,360,448 A | 11/1994 | Thramann |
| 5,366,457 A | 11/1994 | McGuire et al. |
| 5,376,094 A * | 12/1994 | Kline .................... 606/113 |
| 5,383,884 A | 1/1995 | Summers |
| 5,395,188 A | 3/1995 | Bailey et al. |
| 5,395,317 A | 3/1995 | Kambin |
| 5,396,880 A | 3/1995 | Kagan et al. |
| 5,403,276 A | 4/1995 | Schechter et al. |
| 5,415,661 A | 5/1995 | Holmes |
| 5,433,739 A | 7/1995 | Sluijter et al. |
| 5,445,140 A | 8/1995 | Tovey |
| 5,445,639 A | 8/1995 | Kuslich |
| 5,480,440 A | 1/1996 | Kambin |
| 5,484,437 A | 1/1996 | Michelson |
| 5,489,308 A | 2/1996 | Kuslich et al. |
| 5,496,322 A | 3/1996 | Mathews |
| 5,505,732 A | 4/1996 | Michelson |
| 5,514,137 A | 5/1996 | Coutts |
| 5,514,180 A | 5/1996 | Heggeness et al. |
| 5,520,688 A | 5/1996 | Lin |
| 5,534,031 A | 7/1996 | Matsuzaki et al. |
| 5,545,228 A | 8/1996 | Kambin |
| 5,549,679 A | 8/1996 | Kuslich |
| 5,554,163 A | 9/1996 | Shtuman |
| 5,558,674 A | 9/1996 | Heggeness et al. |
| 5,562,736 A | 10/1996 | Ray et al. |
| 5,569,248 A | 10/1996 | Mathews |
| 5,571,189 A | 11/1996 | Kuslich |
| 5,571,190 A | 11/1996 | Ulrich et al. |
| 5,584,887 A | 12/1996 | Kambin |
| 5,591,170 A | 1/1997 | Spievack et al. |
| 5,630,816 A | 5/1997 | Kambin |
| 5,653,708 A | 8/1997 | Howland |
| 5,665,122 A | 9/1997 | Kambin |
| 5,669,909 A | 9/1997 | Zdeblick et al. |
| 5,700,291 A | 12/1997 | Kuslich et al. |
| 5,702,453 A | 12/1997 | Rabbe et al. |
| 5,702,454 A | 12/1997 | Baumgartner |
| 5,702,455 A | 12/1997 | Saggar |
| 5,713,904 A | 2/1998 | Errico et al. |
| 5,720,749 A | 2/1998 | Rupp |
| 5,728,097 A | 3/1998 | Mathews |
| 5,735,899 A | 4/1998 | Schwartz et al. |
| 5,741,253 A | 4/1998 | Michelson |
| 5,741,261 A | 4/1998 | Moskovitz et al. |
| 5,743,912 A | 4/1998 | Lahille et al. |
| 5,762,629 A | 6/1998 | Kambin |
| 5,779,704 A | 7/1998 | Kim |
| 5,785,709 A | 7/1998 | Kummer et al. |
| 5,792,044 A | 8/1998 | Foley et al. |
| 5,792,110 A | 8/1998 | Cunningham |
| 5,827,285 A | 10/1998 | Bramlet |
| 5,827,328 A | 10/1998 | Buttermann |
| 5,885,292 A | 3/1999 | Moskovitz et al. |
| 5,888,220 A | 3/1999 | Felt et al. |
| 5,888,223 A | 3/1999 | Bray, Jr. |
| 5,891,147 A | 4/1999 | Moskovitz et al. |
| 5,902,231 A | 5/1999 | Foley et al. |
| 5,906,616 A | 5/1999 | Pavlov et al. |
| 5,921,971 A | 7/1999 | Agro et al. |
| 5,928,239 A | 7/1999 | Mirza |
| 5,935,131 A | 8/1999 | Bonutti |
| 5,937,524 A | 8/1999 | Hornsby |
| 5,954,635 A | 9/1999 | Foley et al. |
| 5,961,329 A | 10/1999 | Stucki-McCormick |
| 5,964,761 A | 10/1999 | Kambin |
| 5,968,062 A | 10/1999 | Thomas et al. |
| 5,972,015 A | 10/1999 | Scribner et al. |
| 5,976,146 A | 11/1999 | Ogawa et al. |
| 5,976,187 A | 11/1999 | Richelsoph |
| 5,980,504 A | 11/1999 | Sharkey et al. |
| 5,989,256 A | 11/1999 | Kuslich et al. |
| 6,001,101 A | 12/1999 | Augagneur et al. |
| 6,007,487 A | 12/1999 | Foley et al. |
| 6,010,495 A | 1/2000 | Tilton, Jr. |
| 6,010,502 A | 1/2000 | Bagby |
| 6,019,792 A | 2/2000 | Cauthen |
| 6,022,362 A | 2/2000 | Lee et al. |
| 6,030,162 A | 2/2000 | Huebner |
| 6,033,406 A | 3/2000 | Mathews |
| 6,036,696 A | 3/2000 | Lambrecht et al. |
| 6,053,916 A | 4/2000 | Moore |
| 6,056,749 A | 5/2000 | Kuslich |
| 6,066,152 A | 5/2000 | Strauss et al. |
| 6,066,154 A | 5/2000 | Reiley et al. |
| 6,080,099 A | 6/2000 | Slater et al. |
| 6,086,589 A | 7/2000 | Kuslich et al. |
| 6,093,207 A | 7/2000 | Pisharodi |
| 6,095,149 A | 8/2000 | Sharkey et al. |
| 6,120,502 A | 9/2000 | Michelson |
| 6,123,705 A | 9/2000 | Michelson |
| 6,127,597 A | 10/2000 | Beyar et al. |

| | | | | | | |
|---|---|---|---|---|---|---|
| 6,152,871 | A | 11/2000 | Foley et al. | 2003/0158557 A1 | 8/2003 | Cragg et al. |
| 6,159,212 | A | 12/2000 | Schoedinger, III et al. | 2003/0176926 A1 | 9/2003 | Boehm et al. |
| 6,162,170 | A | 12/2000 | Foley et al. | 2003/0181982 A1 | 9/2003 | Kuslich |
| 6,175,758 | B1 | 1/2001 | Kambin | 2003/0191474 A1 | 10/2003 | Cragg et al. |
| 6,176,823 | B1 | 1/2001 | Foley et al. | 2003/0195518 A1 | 10/2003 | Cragg |
| 6,187,000 | B1 | 2/2001 | Davison et al. | 2003/0204189 A1 | 10/2003 | Cragg |
| 6,206,822 | B1 | 3/2001 | Foley et al. | 2004/0138752 A1 | 7/2004 | Michelson |
| 6,206,826 | B1 | 3/2001 | Mathews et al. | 2004/0141827 A1 | 7/2004 | Dicke |
| 6,210,412 | B1 | 4/2001 | Michelson | 2004/0151559 A1 | 8/2004 | Craven |
| 6,217,509 | B1 | 4/2001 | Foley et al. | 2004/0193155 A1 | 9/2004 | Castaneda |
| 6,241,734 | B1 | 6/2001 | Scribner et al. | 2004/0230195 A1 | 11/2004 | Kaikkonen et al. |
| 6,264,656 | B1 | 7/2001 | Michelson | 2005/0038438 A1 | 2/2005 | Anderson et al. |
| 6,287,313 | B1 | 9/2001 | Sasso | 2005/0070908 A1 | 3/2005 | Cragg |
| 6,306,140 | B1 | 10/2001 | Siddiqui | 2005/0101961 A1 | 5/2005 | Huebner et al. |
| 6,315,795 | B1 | 11/2001 | Scarborough et al. | 2005/0107791 A1 | 5/2005 | Manderson |
| 6,319,254 | B1 | 11/2001 | Giet et al. | 2005/0113919 A1 | 5/2005 | Cragg et al. |
| 6,371,990 | B1 | 4/2002 | Ferree | 2005/0113928 A1 | 5/2005 | Cragg et al. |
| 6,379,334 | B1 | 4/2002 | Frassica | 2005/0113929 A1 | 5/2005 | Cragg et al. |
| 6,383,188 | B2 | 5/2002 | Kuslich et al. | 2005/0137601 A1 | 6/2005 | Assell et al. |
| 6,383,190 | B1 | 5/2002 | Preissman | 2005/0137602 A1 | 6/2005 | Assell et al. |
| 6,387,130 | B1 | 5/2002 | Stone et al. | 2005/0137604 A1 | 6/2005 | Assell et al. |
| 6,395,007 | B1 | 5/2002 | Bhatnagar et al. | 2005/0137605 A1 | 6/2005 | Assell et al. |
| 6,402,750 | B1 | 6/2002 | Atkinson et al. | 2005/0137607 A1 | 6/2005 | Assell et al. |
| 6,409,766 | B1 | 6/2002 | Brett | 2005/0137612 A1 | 6/2005 | Assell et al. |
| 6,416,515 | B1 | 7/2002 | Wagner | 2005/0149034 A1 | 7/2005 | Assell et al. |
| 6,419,678 | B1 | 7/2002 | Asfora | 2005/0149049 A1 | 7/2005 | Assell et al. |
| 6,423,095 | B1 | 7/2002 | Van Hoeck et al. | 2005/0149191 A1 | 7/2005 | Cragg et al. |
| 6,436,098 | B1 | 8/2002 | Michelson | 2005/0165406 A1 | 7/2005 | Assell et al. |
| 6,436,140 | B1 | 8/2002 | Liu et al. | 2005/0261695 A1 | 11/2005 | Cragg et al. |
| 6,436,143 | B1 | 8/2002 | Ross et al. | 2006/0058800 A1 | 3/2006 | Ainsworth et al. |
| 6,440,138 | B1 * | 8/2002 | Reiley et al. .................. 606/79 | 2006/0079898 A1 | 4/2006 | Ainsworth et al. |
| 6,447,514 | B1 | 9/2002 | Stalcup et al. | 2006/0155297 A1 | 7/2006 | Ainsworth et al. |
| 6,447,518 | B1 | 9/2002 | Krause et al. | 2006/0206208 A1 | 9/2006 | Michelson |
| 6,447,546 | B1 | 9/2002 | Bramlet et al. | 2006/0206209 A1 | 9/2006 | Cragg et al. |
| 6,447,547 | B1 | 9/2002 | Michelson | 2006/0229622 A1 | 10/2006 | Huebner et al. |
| 6,464,713 | B2 | 10/2002 | Bonutti | 2006/0264957 A1 | 11/2006 | Cragg et al. |
| 6,485,518 | B1 | 11/2002 | Cornwall et al. | 2007/0010717 A1 | 1/2007 | Cragg |
| 6,517,541 | B1 | 2/2003 | Sesic | 2007/0010819 A1 | 1/2007 | Johnstone |
| 6,533,791 | B1 | 3/2003 | Betz et al. | 2007/0055260 A1 | 3/2007 | Cragg |
| 6,540,747 | B1 | 4/2003 | Marino | 2007/0066977 A1 | 3/2007 | Assell et al. |
| 6,558,386 | B1 | 5/2003 | Cragg | 2007/0093847 A1 | 4/2007 | Scribner et al. |
| 6,558,390 | B2 | 5/2003 | Cragg | 2007/0112351 A1 | 5/2007 | Assell et al. |
| 6,562,046 | B2 | 5/2003 | Sasso | 2007/0118132 A1 | 5/2007 | Culbert et al. |
| 6,575,979 | B1 | 6/2003 | Cragg | 2007/0167951 A1 | 7/2007 | Ainsworth et al. |
| 6,607,530 | B1 | 8/2003 | Carl et al. | 2007/0168036 A1 | 7/2007 | Ainsworth et al. |
| 6,610,091 | B1 | 8/2003 | Reiley | 2007/0233099 A1 | 10/2007 | Cragg |
| 6,740,090 | B1 * | 5/2004 | Cragg et al. .................. 606/80 | 2007/0233260 A1 | 10/2007 | Cragg |
| 6,790,210 | B1 | 9/2004 | Cragg et al. | 2007/0260270 A1 | 11/2007 | Assell et al. |
| 6,875,215 | B2 | 4/2005 | Taras et al. | 2007/0265652 A1 | 11/2007 | Assell |
| 6,899,716 | B2 | 5/2005 | Cragg | 2008/0004707 A1 | 1/2008 | Cragg |
| 6,921,403 | B2 | 7/2005 | Cragg et al. | 2008/0065076 A1 | 3/2008 | Cragg |
| 6,991,653 | B2 | 1/2006 | White et al. | 2008/0065080 A1 | 3/2008 | Assell et al. |
| 7,014,633 | B2 | 3/2006 | Cragg | 2008/0065092 A1 | 3/2008 | Assell et al. |
| 7,033,394 | B2 | 4/2006 | Michelson | 2008/0065093 A1 | 3/2008 | Assell et al. |
| 7,037,309 | B2 | 5/2006 | Weil et al. | 2008/0065094 A1 | 3/2008 | Assell et al. |
| 7,087,056 | B2 | 8/2006 | Vaughan | 2008/0071278 A1 | 3/2008 | Assell et al. |
| 7,087,058 | B2 | 8/2006 | Cragg | 2008/0071282 A1 | 3/2008 | Assell et al. |
| 7,309,338 | B2 | 12/2007 | Cragg | 2008/0091199 A1 | 4/2008 | Cragg |
| 7,329,259 | B2 | 2/2008 | Cragg | 2008/0097452 A1 | 4/2008 | Assell et al. |
| 2002/0022888 A1 | | 2/2002 | Serhan et al. | 2008/0154275 A1 | 6/2008 | Assell et al. |
| 2002/0032444 A1 | | 3/2002 | Mische | 2008/0188895 A1 | 8/2008 | Cragg |
| 2002/0038123 A1 | | 3/2002 | Visotsky et al. | 2008/0262502 A1 | 10/2008 | Ainsworth et al. |
| 2002/0052608 A1 | | 5/2002 | Kvarnstrom et al. | 2008/0262555 A1 | 10/2008 | Assell |
| 2002/0072801 A1 | | 6/2002 | Michelson | | | |
| 2002/0077632 A1 | | 6/2002 | Tsou | | | |
| 2002/0077700 A1 | | 6/2002 | Varga et al. | FOREIGN PATENT DOCUMENTS | | |
| 2002/0077702 A1 | | 6/2002 | Castro | EP | 0 611 116 B1 | 4/1994 |
| 2002/0107573 A1 | | 8/2002 | Steinberg | EP | 0 980 677 A1 | 2/2000 |
| 2002/0110439 A1 | | 8/2002 | Craven | WO | WO 95/22285 | 8/1995 |
| 2002/0147485 A1 | | 10/2002 | Mamo et al. | WO | WO 97/40878 | 11/1997 |
| 2003/0028193 A1 | | 2/2003 | Weil et al. | WO | WO 98/02201 | 1/1998 |
| 2003/0045881 A1 | | 3/2003 | Barouk et al. | WO | WO 98/17190 | 4/1998 |
| 2003/0065394 A1 | | 4/2003 | Michelson | WO | WO 98/38918 | 9/1998 |

| WO | WO 99/47055 | 9/1999 |
| WO | WO 99/51149 | 10/1999 |
| WO | WO 00/53077 | 9/2000 |
| WO | WO 00/67650 | 11/2000 |
| WO | WO 01/28468 A1 | 4/2001 |
| WO | WO 01/60268 A1 | 8/2001 |
| WO | WO 02/09801 A1 | 2/2002 |
| WO | WO 02/13732 A2 | 2/2002 |
| WO | WO 02/34120 A2 | 5/2002 |
| WO | WO 02/058599 A2 | 8/2002 |

OTHER PUBLICATIONS

R. Johnsson et al., "Posterolateral lumbar fusion using facet joint fixation with biodegradable rods: a pilot study", Eur Spine J., (1997) 6: 144-148.
R.P. Louis, Md., "Anatomy, Physiology, and Biomechanics of the Lumbopelvic Junction", Lumbosacral and Spinopelvic Fusion, Chapter 1 (pp. 1-11) Lippincott-Raven Pub. (1996).
M.R. Zindrick, MD et al., "Clinical Anatomy of the Lumbrosacral Junction and Pelvis" Lumbrosacral and Spinopelvic Fusion, Chapt. 2 (pp. 13-25) Lippincott-Raven Pub. (1996).
J.W. Olgilvie, MD et al., "Overview of Fixation to the Sacrum & Pelvis in Spinal Surgery", Lumbosacral and Spinopelvic Fusion, Chapter 17 (pp. 199-208). Lippincott-Raven Pub. (1996).
S.A. Caruso, ME et al., "Instrumented Fusions of the Lumbosacral Spine: A Technical Overview", Lumbosacral and Spinopelvic Fusion, Chapter 18 (pp. 199-210) Lippincott-Raven Pub. (1996).
R.P. Louis, MD, "Lumbopelvic Fusion", Lumbosacral and Spinopelvic Fusion, Chapter 38 (pp. 4790492) Lippincott-Raven Pub. (1996).
J. Dove, FRCS, "The Hartshill System for the Front of the Lumbosacral Spine", Lumbo-sacral and Spinopelvic Fusion, Chapter 42 (pp. 539-543) Lippincott-Raven Pub. (1996).
P. Kambin, MD et al., "Arthoscopic Fusion of the Lumbosacral Spine", Lumbosacral and Spinopelvic Fusion, Chapter 44 (pp. 565-577) Lippincott-Raben Pub. (1996).
Jason A. Smith, MD et al., "Clinical Outcome of Trans-Sacral Interbody Fusion After Partial Reduction for High-Grade L5-S1 Spondylolisthesis," Spine 2001, vol. 26, No. 20, pp. 2227-2234.
Michael MacMilland; MD et al., "Percutaneous Lumbosacarl Fixation and Fusion," Percutaneous Spine Techniques, Jan. 1996, vol. 7, No. 1, pp. 99-1-6.
Curtis A. Dickman, M.D., et al., "Transpedicular screw-rod fixation of the lumber spine: operative technique and outcome in 104 cases," J. Neurosurg, Dec. 1992, vol. 77, pp. 860-870.
Richard M. Slone, MD et al., "Spinal Fixation, Part 1, Basic Hardware, and Fixation Techniques for the Cervical Spine," RadioGraphics, 1993, vol. 13, No. 2, pp. 341-356.
Richard M. Slone, MD et al., "Spinal Fixation, Part 2, Fixation Techniques and Hardware for the Thoracic and Lumbosacral Spine," RadioGraphics, 199., vol. 13, No. 3, pp. 521-543.
Michael MacMillan, et al., "Biomechanical Analysis of a New Anterior Spine Implant for Post-Corpectomy Instability," Journal of Spinal Disorders, 1995, vol. 8, No. 1, pp. 56-61.
B. Jeanneret, et al., "Posterior Stabilization in L5-S1 Isthmick Spondylolisthesis with Paralaminar Screw Fixation: Anatomical and Clinical Results," Journal of Spinal Disorders, vol. 9, No. 3, pp. 223-233 (1996) Lippincott-Raven Publishers, Philadelphia.
Hallett H. Mathews, M.D., "minimally Invasive Fusion Techniques, Percutaneous Interbody Fusions," Orthopedic Clinics of North America, Oct. 1998, vol. 29, No. 4.
Parviz Kambin, M.D., et al, "Arthoscopic Microdiscectomy: An Alternative to Open Disc Surgery," *The Mount Sinai Journal of Medicine*, Sep. 2000, vol. 67, No. 4.
Hallett H. Mathews, M.D., et al., "Perspectives on Modern Orthopaedics, Minimally Invasive Techniques for the Treatment of Intervertebral Disk Herniation," *Journal of the American Academy of Orthopaedic Surgeons*, Mar./Apr. 2002, vol. 10, No. 2.
Parviz Kambin, M.D., "Percutaneous Spine Techniques, Diagnostic and Therapeutic Spinal Arthroscopy," *Neurosurgery Clinics of North America*, Jan. 1996, vol. 7, No. 1.
Parviz Kambin, M.D., et al., "Arthoscopic Discectomy of the Lumbar Spine," *Clinical Orthopaedics and Related Research*, Apr. 1997, No. 337.
U.S. Appl. No. 2002/0082598 A1, *Percutaneous Vertebral Fusion System*, published Jun. 27, 2002.
U.S. Appl. No. 2002/0068939 A1, *Expandable Orthopedic Device*, published Jun. 6, 2002.
John L. Emmett, M.D., M.S. (Urology), David M. Witten, M.D., M.S. (Radiology)—vol. 1, Third Edition—Clinical Urography—An Atlas And Textbook Of Roentgenologic Diagnosis-1971-Phneumography (Retroperitoneal Gas [Air] Insufflation; Perirenal Insufflation; Presacral Insufflation).
Supplementary European Search Report mailed on Feb. 1, 2007 for PCT/US0104744.
Friedrich W. Rathke and Karl F. Schlegel, Surgery of the Spine, Atlas of Orthopaedic Operations, vol. 1, 1979, pp. 222-224.
U.S. Appl. No. 11/940,208, filed Nov. 14, 2007, Assell, et al.
U.S. Appl. No. 11/940,252, filed Nov. 14, 2007, Assell, et al.
U.S. Appl. No. 11/940,265, filed Nov. 14, 2007, Assell, et al.
U.S. Appl. No. 11/942,470, filed Nov. 19, 2007, Assell, et al.
U.S. Appl. No. 11/942,488, filed Nov. 19, 2007, Assell, et al.
U.S. Appl. No. 11/942,547, filed Nov. 19, 2007, Assell, et al.
U.S. Appl. No. 11/953,724, filed Dec. 10, 2007, Assell, et al.
European Patent Office Communication pursuant to Art. 94(3) EPC dated Jul. 14, 2008 for Euoprean App. 01910676.4, WO 01/60262.
Schreiber, A. And Leu, Hj., "Percutaneous Nucleotomy: Technique with Discoscopy," Orthopedics, Apr. 1991, vol. 14, No. 4, pp. 439-446.
Schreiber, Adam et al. "Does Percutaneous Nucleotomy With Discoscopy Replace Conventional Discectomy?," Clinical Orthopaedics and Related Research, No. 238, Jan. 1989, pp. 35-42.
Translation of Japanese Office Action mailed Aug. 27, 2008 in Japanese Patent App. No. 2001-559362.

* cited by examiner

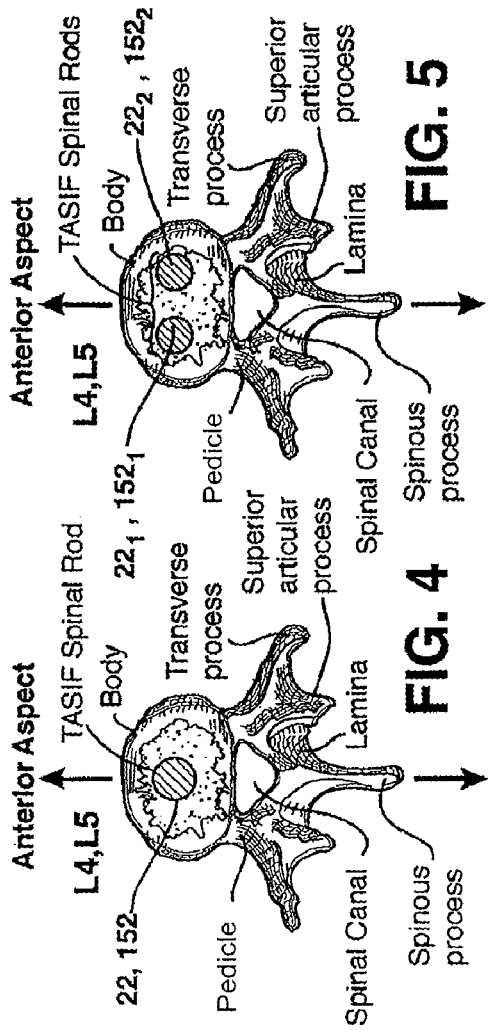
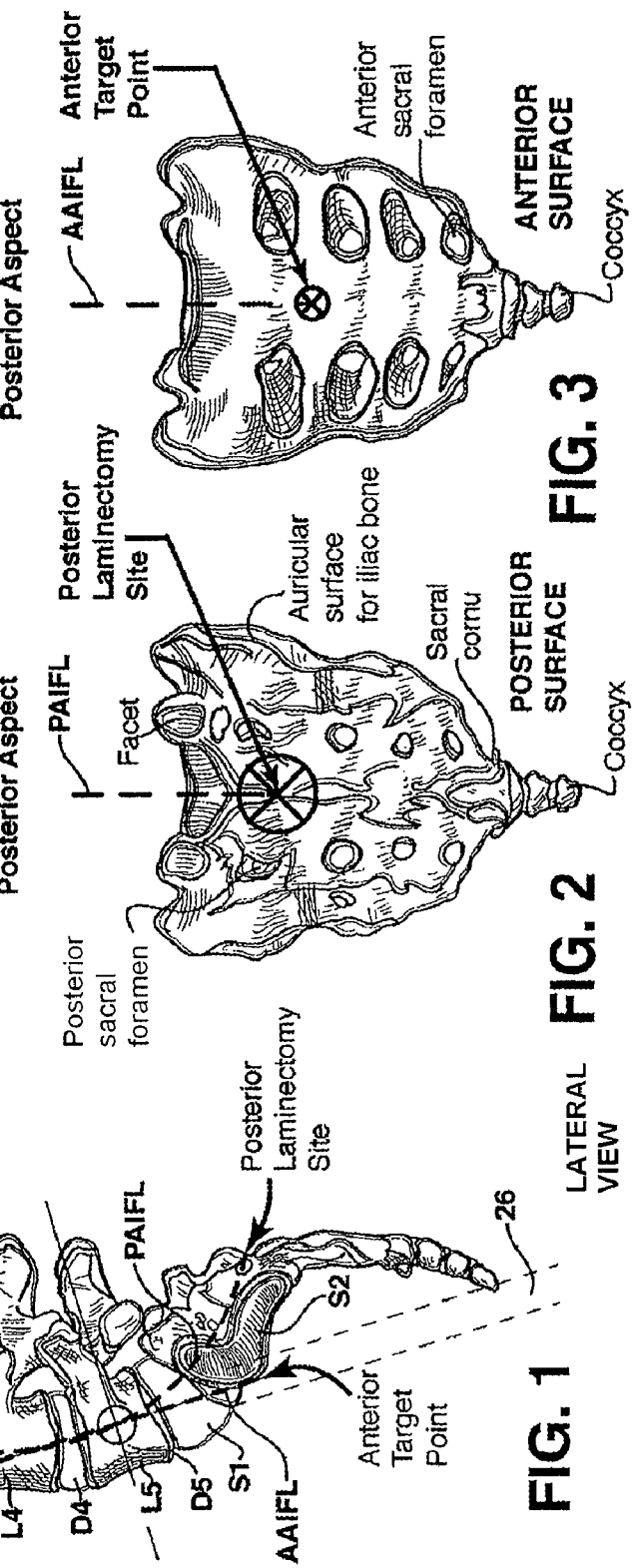
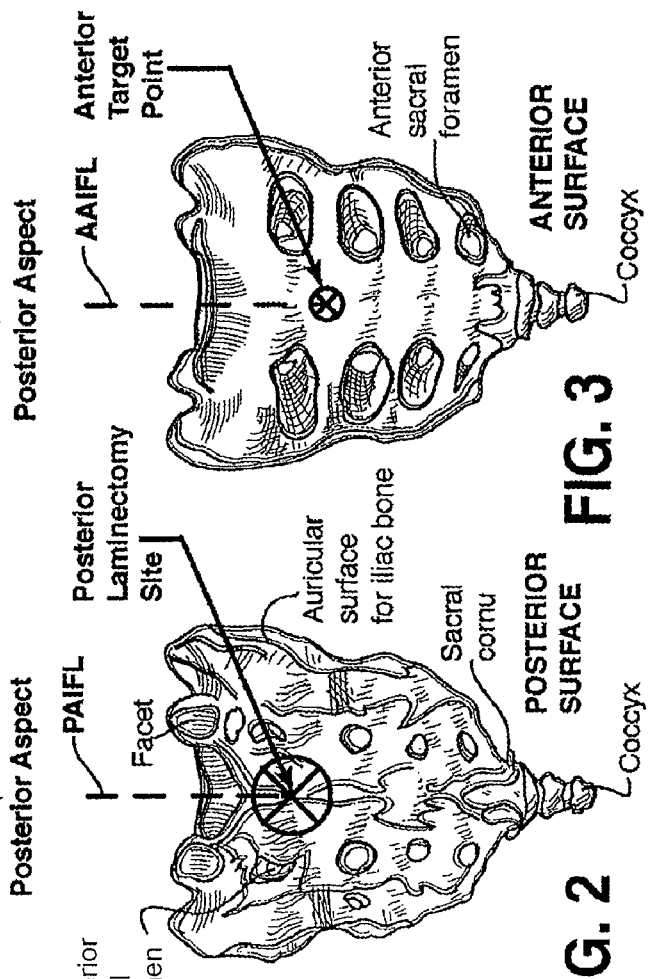
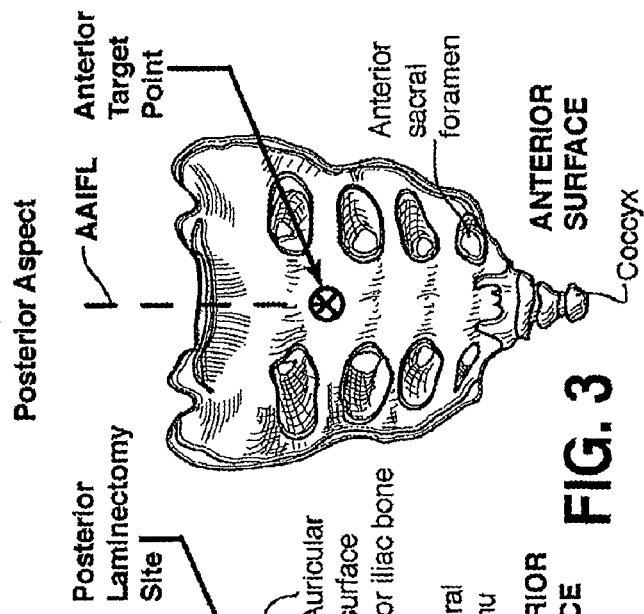

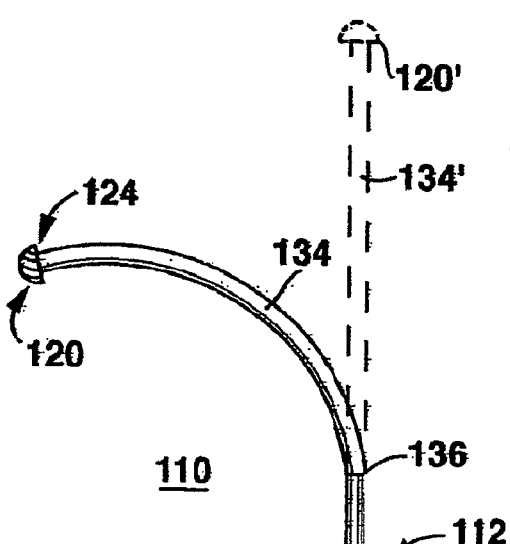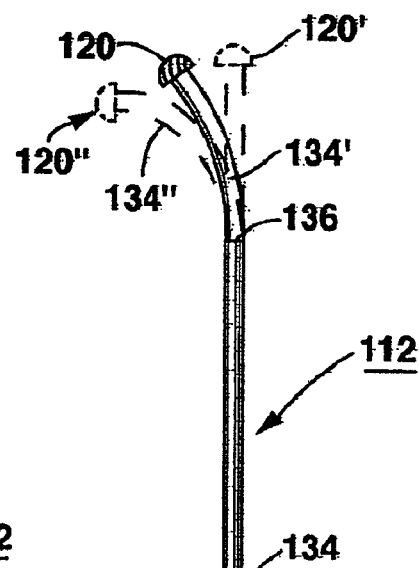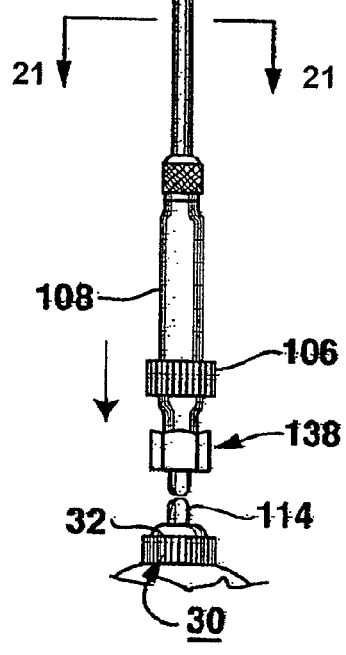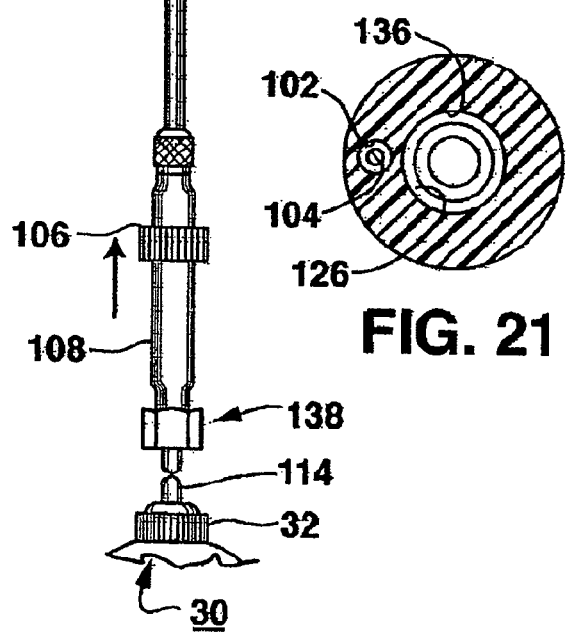
FIG. 19
FIG. 20
FIG. 21

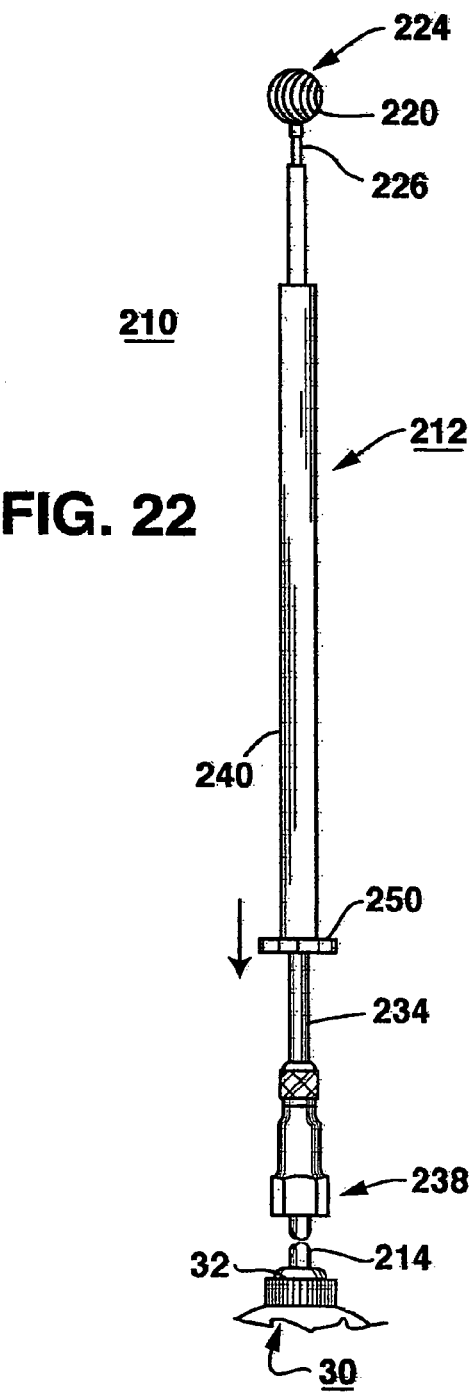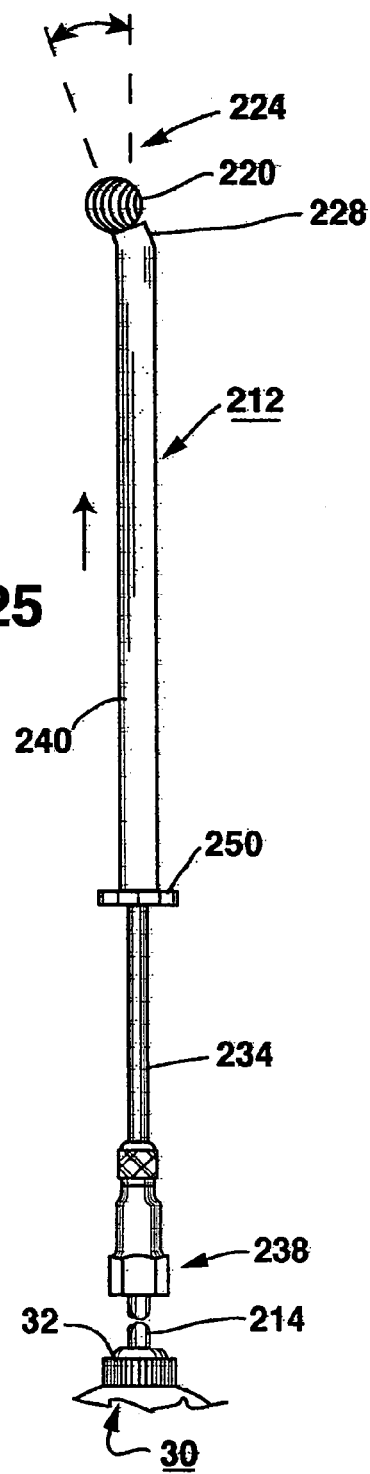

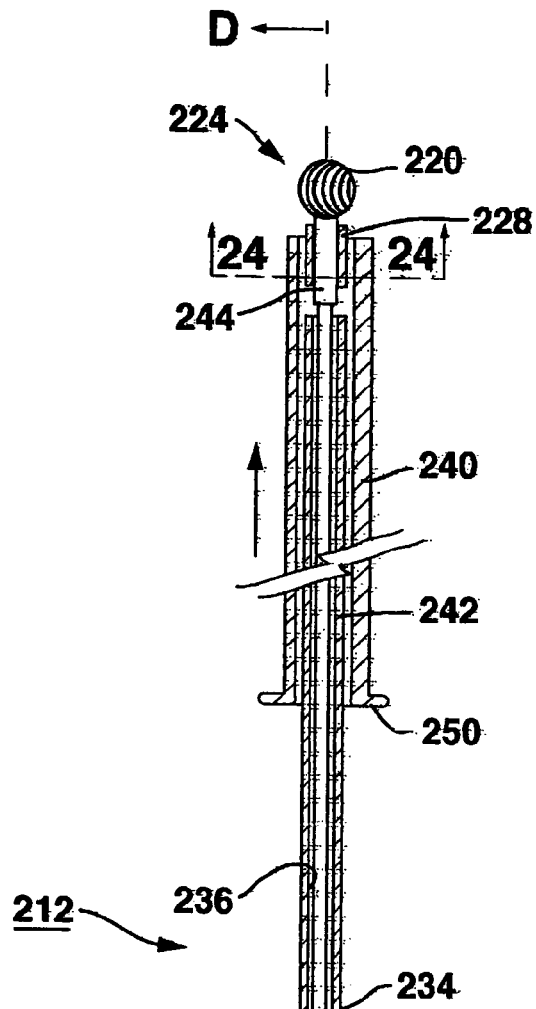
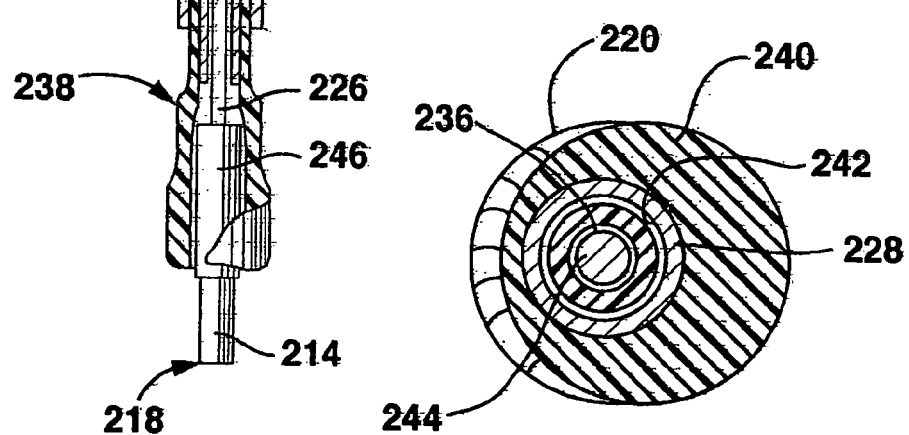
FIG. 23
FIG. 24

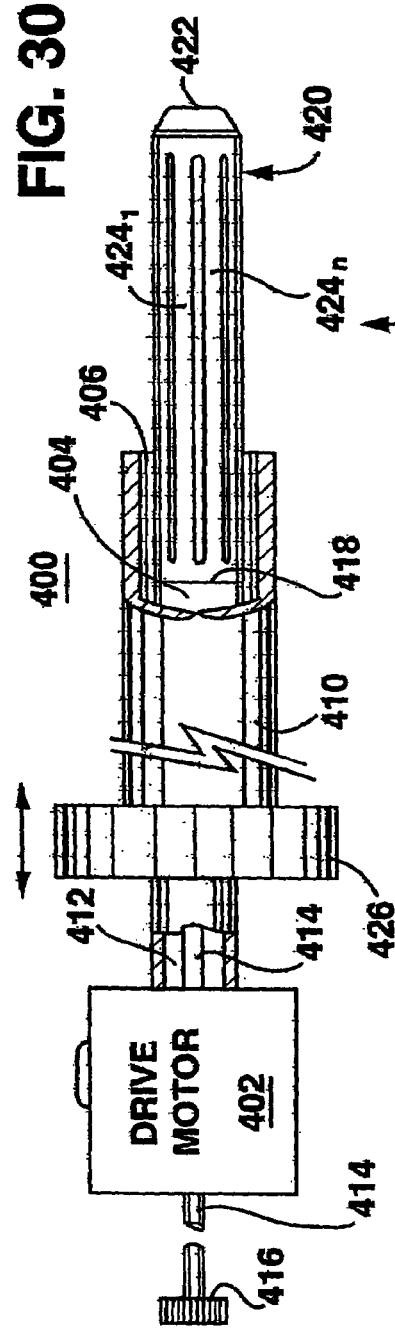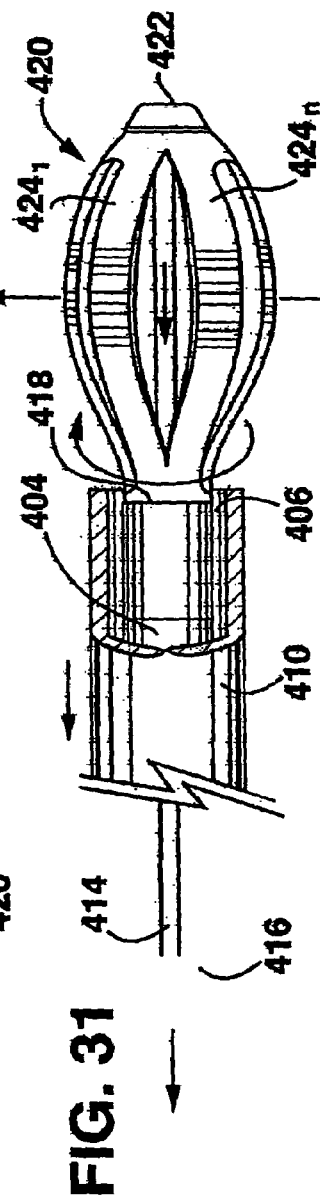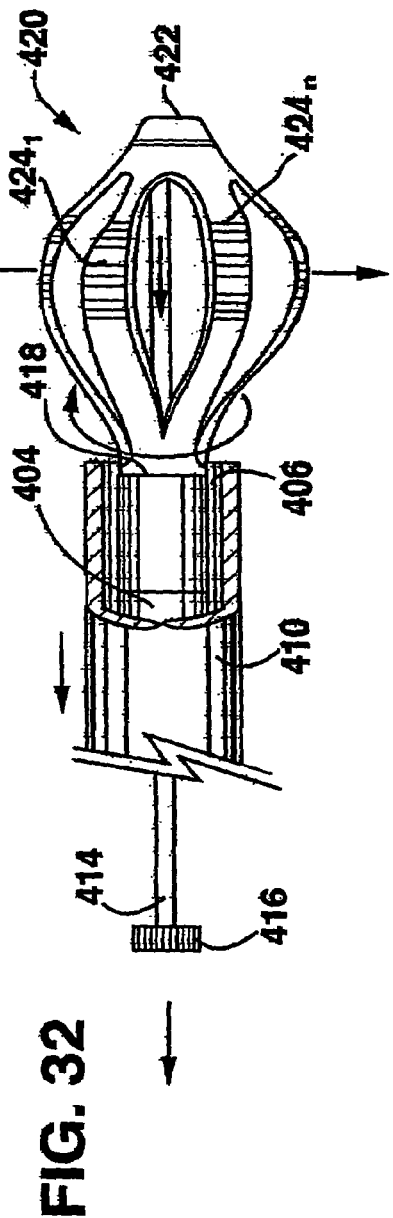

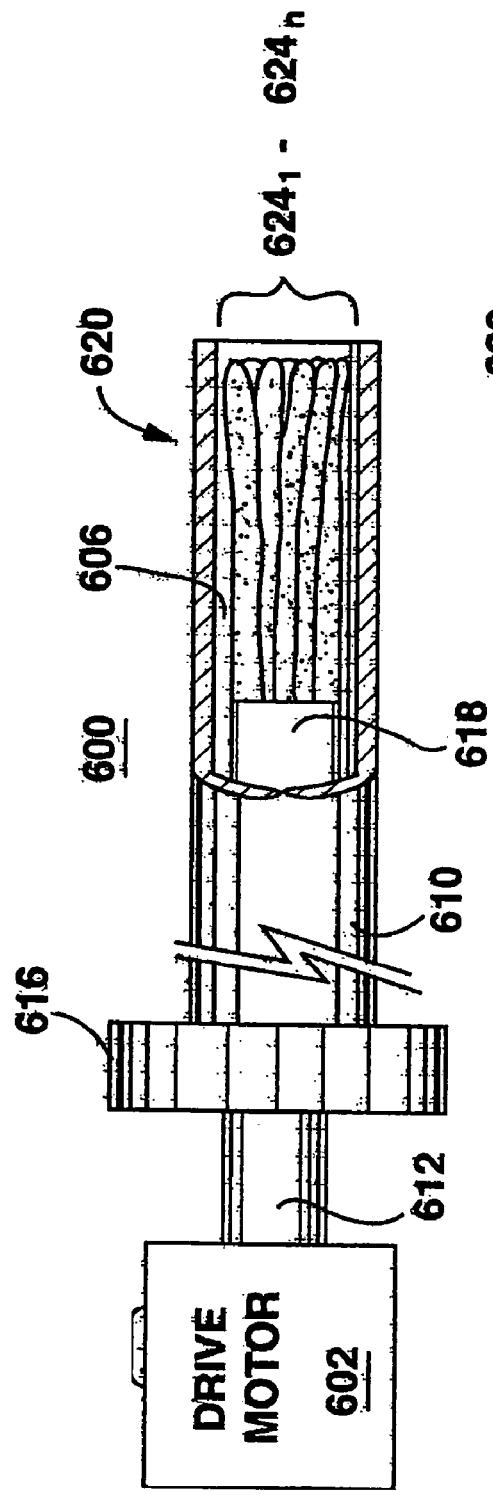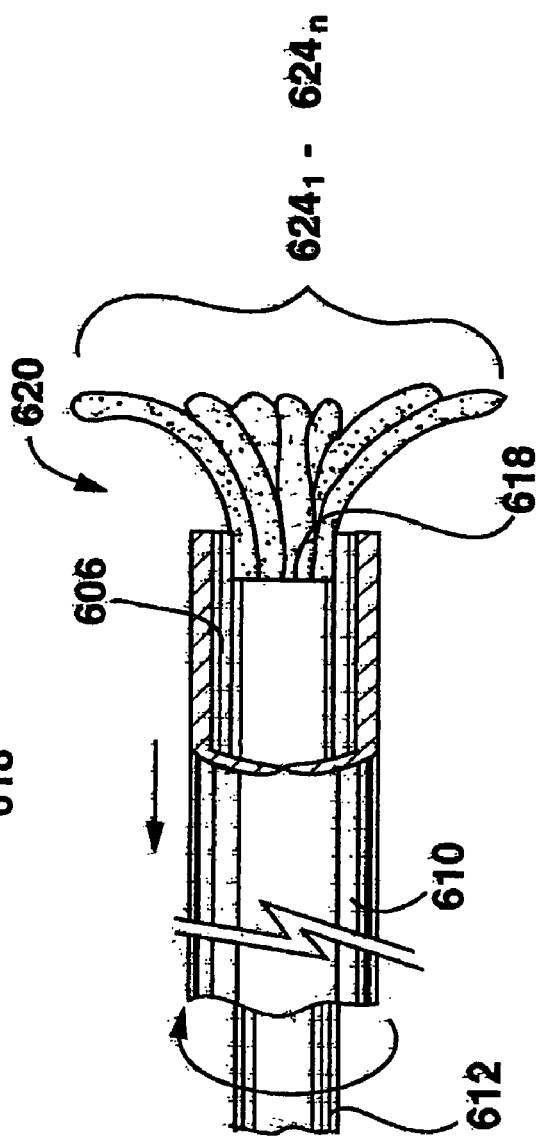

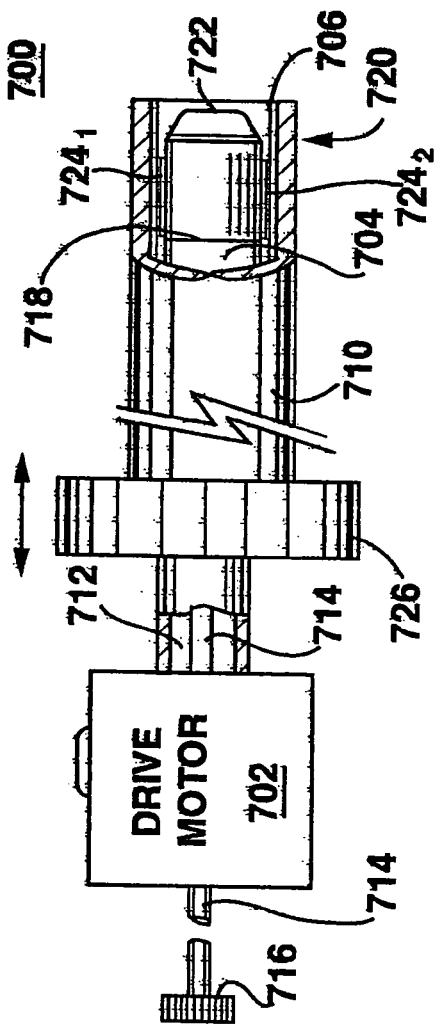
FIG. 37
FIG. 38
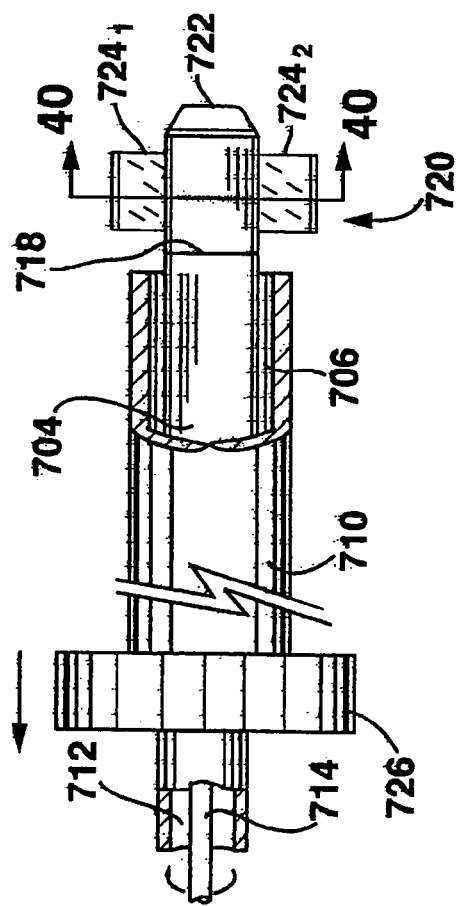
FIG. 39
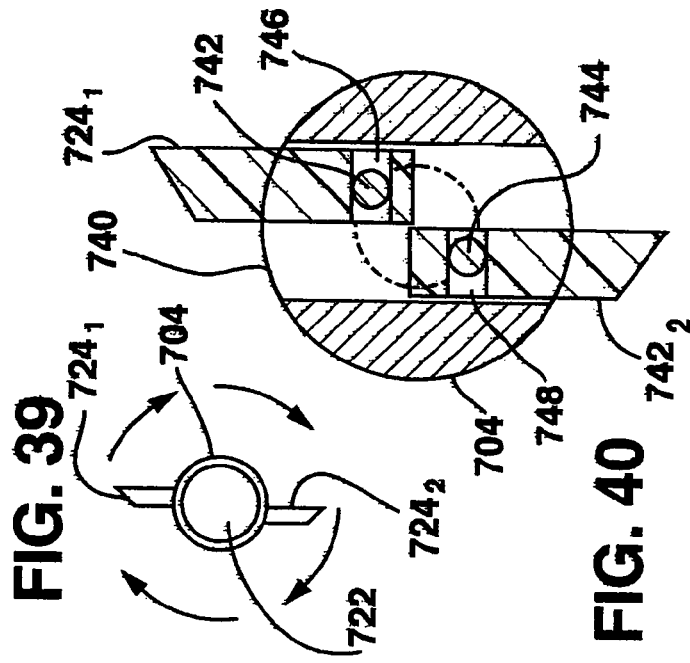
FIG. 40

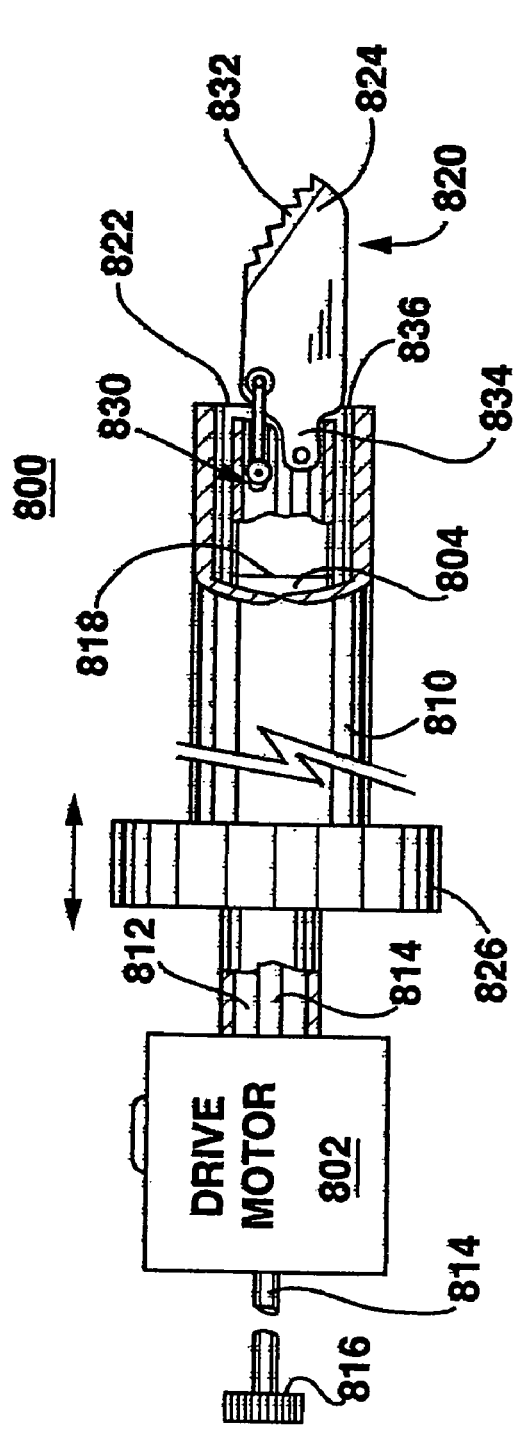
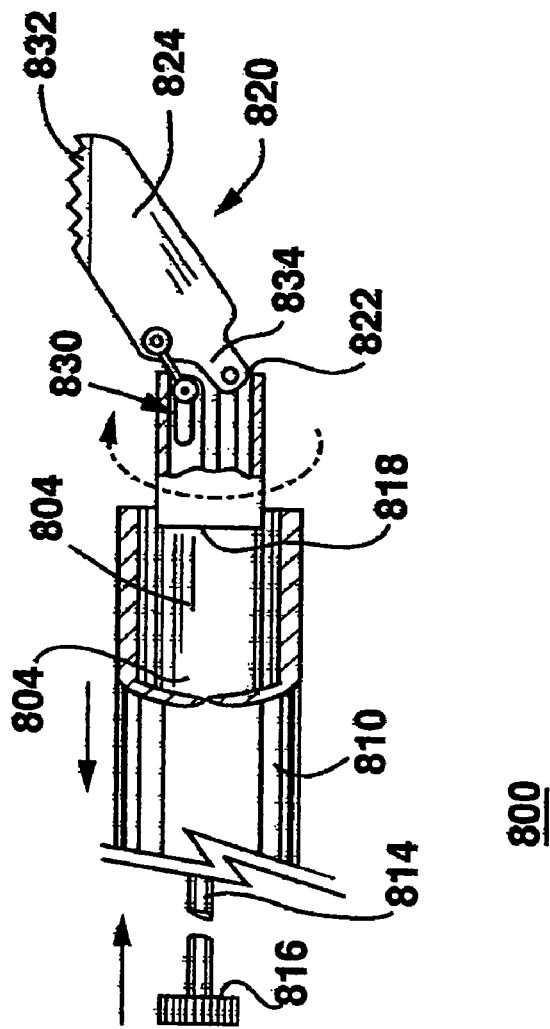
FIG. 41
FIG. 42

METHODS AND APPARATUS FOR FORMING SHAPED AXIAL BORES THROUGH SPINAL VERTEBRAE

This is a continuation application of U.S. patent application Ser. No. 09/710,369, filed on Nov. 10, 2000, titled METHODS AND APPARATUS FOR FORMING SHAPED AXIAL BORES THROUGH SPINAL VERTEBRAE, which issued as U.S. Pat. No. 6,740,090 on May 25, 2004; which claims priority and benefits from Provisional Patent Application No. 60/182,748, filed Feb. 16, 2000, titled METHOD AND APPARATUS FOR TRANS-SACRAL SPINAL FUSION.

CROSS-REFERENCE TO RELATED APPLICATIONS

Reference is hereby made to commonly assigned U.S. patent application Ser. Nos. (1) Ser. No. 09/640,222, filed Aug. 16, 2000, titled METHOD AND APPARATUS FOR PROVIDING POSTERIOR OR ANTERIOR TRANS-SACRAL ACCESS TO SPINAL VERTEBRAE, which issued as U.S. Pat. No. 6,575,979 on Jun. 10, 2003; (2) Ser. No. 09/684,820, filed Oct. 10, 2000, titled AXIAL SPINAL IMPLANT AND METHOD AND APPARATUS FOR IMPLANTING AN AXIAL SPINAL IMPLANT WITHIN THE VERTEBRAE OF THE SPINE, which issued as U.S. Pat. No. 6,558,386 on May 6, 2003; and (3) Ser. No. 09/709,105, filed on Nov. 10, 2000, titled METHODS AND APPARATUS FOR FORMING CURVED AXIAL BORES THROUGH SPINAL VERTEBRAE which issued as U.S. Pat. No. 6,790,210 on Sep. 14, 2004.

FIELD OF THE INVENTION

The present invention relates generally to spinal surgery, particularly methods and apparatus for forming one or more shaped axial bore through vertebral bodies in general alignment with a visualized, trans-sacral axial instrumentation/fusion (TASIF) line in a minimally invasive, low trauma, manner.

BACKGROUND OF THE INVENTION

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or back bone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1-L5 in descending order. The next lower succeeding five vertebrae below the lumbar vertebrae are referred to as the sacral vertebrae and are numbered S1-S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by intervertebral discs formed of fibrous cartilage enclosing a central mass, the nucleus pulposus that provides for cushioning and dampening of compressive forces to the spinal column. The intervertebral discs are anterior to the vertebral canal. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement.

The relatively large vertebral bodies located in the anterior portion of the spine and the intervertebral discs provide the majority of the weight bearing support of the vertebral column. Each vertebral body has relatively strong bone comprising the outside surface of the body and weak bone comprising the center of the vertebral body.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine) and other disorders, such as ruptured or slipped discs, degenerative disc disease, fractured vertebra, and the like. Patients who suffer from such conditions usually experience extreme and debilitating pain and often neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. Surgical procedures have been developed and used to remove the disc and fuse the vertebral bodies together and/or to stabilize the intervertebral structures. Although damaged discs and vertebral bodies can be identified with sophisticated diagnostic imaging, the surgical procedures are so extensive that clinical outcomes are not consistently satisfactory. Furthermore, patients undergoing presently available fusion surgery experience significant complications and uncomfortable, prolonged convalescence.

A number of devices and techniques involving implantation of spinal implants to reinforce or replace removed discs and/or anterior portions of vertebral bodies and which mechanically immobilize areas of the spine assisting in the eventual fusion of the treated adjacent vertebrae have also been employed or proposed over the years In order to overcome the disadvantages of purely surgical techniques. Such techniques have been used effectively to treat the above described conditions and to relieve pain suffered by the patient. However, there are still disadvantages to the present fixation implants and surgical implantation techniques. The historical development of such implants is set forth in U.S. Pat. Nos. 5,505,732, 5,514,180, and 5,888,223, for example.

One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a variation of this technique disclosed in U.S. Pat. Nos. 4,553,273 and 4,636,217, both described in U.S. Pat. No. 5,735,899, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '899 patent, an anterior approach is made, slots are created in the upper and lower vertebrae, and rod ends are fitted into the slots and attached to the remaining vertebral bodies of the upper and lower vertebrae by laterally extending screws.

A number of disc shaped replacements or artificial disc implants and methods of insertion have been proposed as disclosed, for example, in U.S. Pat. Nos. 5,514,180 and 5,888,223, for example. A further type of disc reinforcement or augmentation implant that has been clinically employed for spinal fusion comprises a hollow cylindrical titanium cage that is externally threaded and is screwed laterally into place in a bore formed in the disc between two adjacent vertebrae. Bone grafts from cadavers or the pelvis or substances that promote bone growth are then packed into the hollow center of the cage to encourage bone growth (or ingrowth) through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The large hole or holes can compromise the integrity of the vertebral bodies, and if drilled too posteriorly, can injure the spinal cord. The end plates of the vertebral bodies, which comprise very hard bone and help to give the vertebral bodies needed strength, are usually destroyed during the drilling. The cylindrical cage or cages are now harder than the remaining bone of the vertebral bodies, and the vertebral bodies tend to collapse or "telescope," together. The telescoping causes the length of the vertebral column to shorten and can cause damage to the spinal cord and nerves that pass between the two adjacent vertebrae.

Methods and apparatus for accessing the discs and vertebrae by lateral surgical approaches are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures.

A compilation of the above described surgical techniques and spinal implants and others that have been used clinically is set forth in certain chapters of the book entitled *Lumbosacral and Spinopelvic Fixation*, edited by Joseph Y. Margolies et al. (Lippincott-Raven Publishers, Philadelphia, 1996). Attention is directed particularly to Chapters 1, 2, 17, 18, 38, 42 and 44. In "Lumbopelvic Fusion" (Chapter 38, by Prof. Rene P. Louis, Md.) techniques for repairing a spondylolisthesis, in this case, a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. When the screw is used, bone growth material, e.g., bone harvested from the patient, is inserted into the bore alongside the screw, and the disc space is filled with bone sutured to the screw to keep it in place between the vertebral surfaces to act as a spacer implant occupying the extracted disc between L5 and S1. External bridge plates or rods are also optionally installed. The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

A similar anterior approach for treating spondylolisthesis is disclosed in U.S. Pat. No. 6,056,749. In this approach, a bore hole is formed in a cephalad vertebral body and extends through the intervening disc into a caudal vertebral body, the disc is removed, a disk cage is inserted laterally into the disc space, and an elongated, hollow threaded shaft is inserted into the bore and through a hole in the disc cage. The disk cage takes the place of the harvested bone disc inserts and its interlocking intersection with the shaft takes the place of the sutures employed to tie the harvested bone disc inserts to the screw in the technique described in the above-referenced Chapter 38 publication.

The above-described spinal implant approaches involve highly invasive surgery that laterally exposes the anterior or posterior portions of the vertebrae to be supported or fused.

Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages. It is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

Drilling tools are employed in many of the above described surgical procedures to bore straight holes into the vertebral bones. The boring of curved bores in other bones is described in U.S. Pat. Nos. 4,265,231, 4,541,423, and 5,002,546, for example. The '231 patent describes an elongated drill drive shaft enclosed within a pre-curved outer sheath that is employed to drill curved suture holding open ended bores into bones so that the suture passes through both open ends of the bore. The '423 patent describes an elongated flexible drill drive shaft enclosed within a malleable outer sheath that can be manually shaped into a curve before the bore is formed. The '546 patent describes a complex curve drilling tool employing a pivotal rocker arm and curved guide for a drill bit for drilling a fixed curve path through bone. All of these approaches dictate that the curved bore that is formed follow the predetermined and fixed curvature of the outer sheath or guide. The sheath or guide is advanced through the bore as the bore is made, making it not possible for the user to adjust the curvature of the bore to track physiologic features of the bone that it traverses.

SUMMARY OF THE INVENTION

The preferred embodiments of the invention involve methods and apparatus for forming one or more axial bore through spinal vertebral bodies for performing surgical procedures for receiving spinal implants, or for other medical reasons wherein the axial bore is shaped with one or more recess adapted to anchor spinal implants or receive material dispensed therein or for other purposes.

The preferred embodiments of the present invention involve methods and apparatus including surgical tool sets for first forming an anterior or posterior TASIF axial bore(s) extending from a respective anterior or posterior target point of an anterior or posterior sacral surface through at least one sacral vertebral body and one or more lumbar vertebral body in the cephalad direction. Then, further bore enlarging tools are employed to enlarge one or more selected section of the anterior or posterior TASIF axial bore(s), e.g., the cephalad bore end or a disc space along the bore, so as to provide a recess therein. The recess can be employed for various purposes, e.g., to provide anchoring surfaces for spinal implants inserted into the anterior or posterior TASIF axial bore(s), or to received materials placed into the recess formed in a disc space or vertebral body.

To form an axial bore, the anterior target point on the anterior sacral surface is accessed using a percutaneous tract extending from a skin incision through presacral space. The posterior target point on the posterior sacral surface is accessed using a surgical exposure of the posterior sacral surface. An anterior axial instrumentation/fusion line (AAIFL) or a posterior axial instrumentation/fusion line (PAIFL) that extends from the anterior or posterior target point, respectively, in the cephalad direction following the spinal curvature through one or more vertebral body is visualized by radiographic or fluoroscopic equipment. Preferably, curved anterior or posterior TASIF axial bores are formed in axial or parallel alignment with the visualized AAIFL or PAIFL, respectively, although the invention is not confined to curved axial bores.

When a single anterior or posterior TASIF axial bore is formed, it can be formed in axial or parallel alignment with the visualized axial AAIFL and PAIFL. Similarly, multiple anterior or posterior TASIF axial bores can be formed all in parallel alignment with the visualized axial AAIFL and PAIFL or with at least one such TASIF axial bore formed in axial alignment with the visualized axial AAIFL and PAIFL.

Moreover, multiple anterior or posterior TASIF axial bores can be formed all commencing at the anterior or posterior target point and extending in the cephalad direction with each TASIF axial bore diverging apart from the other and away from the visualized axial AAIFL and PAIFL. The diverging TASIF axial bores terminate as spaced apart locations in a cephalad vertebral body or in separate cephalad vertebral bodies.

In certain embodiments, small diameter anterior and posterior TASIF axial bore forming tools can be employed in the same manner to form pilot holes extending in the cephalad direction through one or more sacral and lumbar vertebral bodies in alignment with the visualized AAIFL and PAIFL. The pilot holes can be used as part of anterior and posterior percutaneous tracts that are subsequently enlarged to form the anterior and posterior TASIF axial bores.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 1-3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of lumbar vertebrae depicting a TASIF spinal implant or rod within a TASIF axial bore formed following the visualized PAIFL or AAIFL of FIGS. 1-3;

FIG. 5 is a sagittal caudal view of lumbar vertebrae depicting a plurality, e.g., 2, TASIF spinal implants or rods within a like plurality of TASIF axial bores formed in parallel with the visualized PAIFL or AAIFL of FIGS. 1-3;

FIGS. 19-21 illustrate a further exemplary boring tool embodiment comprising an elongated drill shaft assembly and drill motor for forming a curved anterior or posterior TASIF axial bore in the manner illustrated in FIGS. 10-18;

FIGS. 22-25 illustrate a still further exemplary boring tool embodiment comprising an elongated drill shaft assembly and drill motor for forming a curved anterior or posterior TASIF axial bore in the manner illustrated in FIGS. 10-18;

FIGS. 30-32 depict a first exemplary embodiment of a counterbore tool for forming an anchoring recess of the type depicted in FIG. 29;

FIGS. 35-36 depict a third exemplary embodiment of a counterbore tool for forming an anchoring recess of the type depicted in FIG. 29;

FIGS. 37-40 depict a fourth exemplary embodiment of a counterbore tool for forming an anchoring recess of the type depicted in FIG. 29; and FIGS. 41-42 depict a second exemplary embodiment of a counterbore tool for forming an anchoring recess of the type depicted in FIG. 29.

DETAILED DESCRIPTION OF THE PREFERRED EMBODIMENTS OF THE INVENTION

Figure 6:
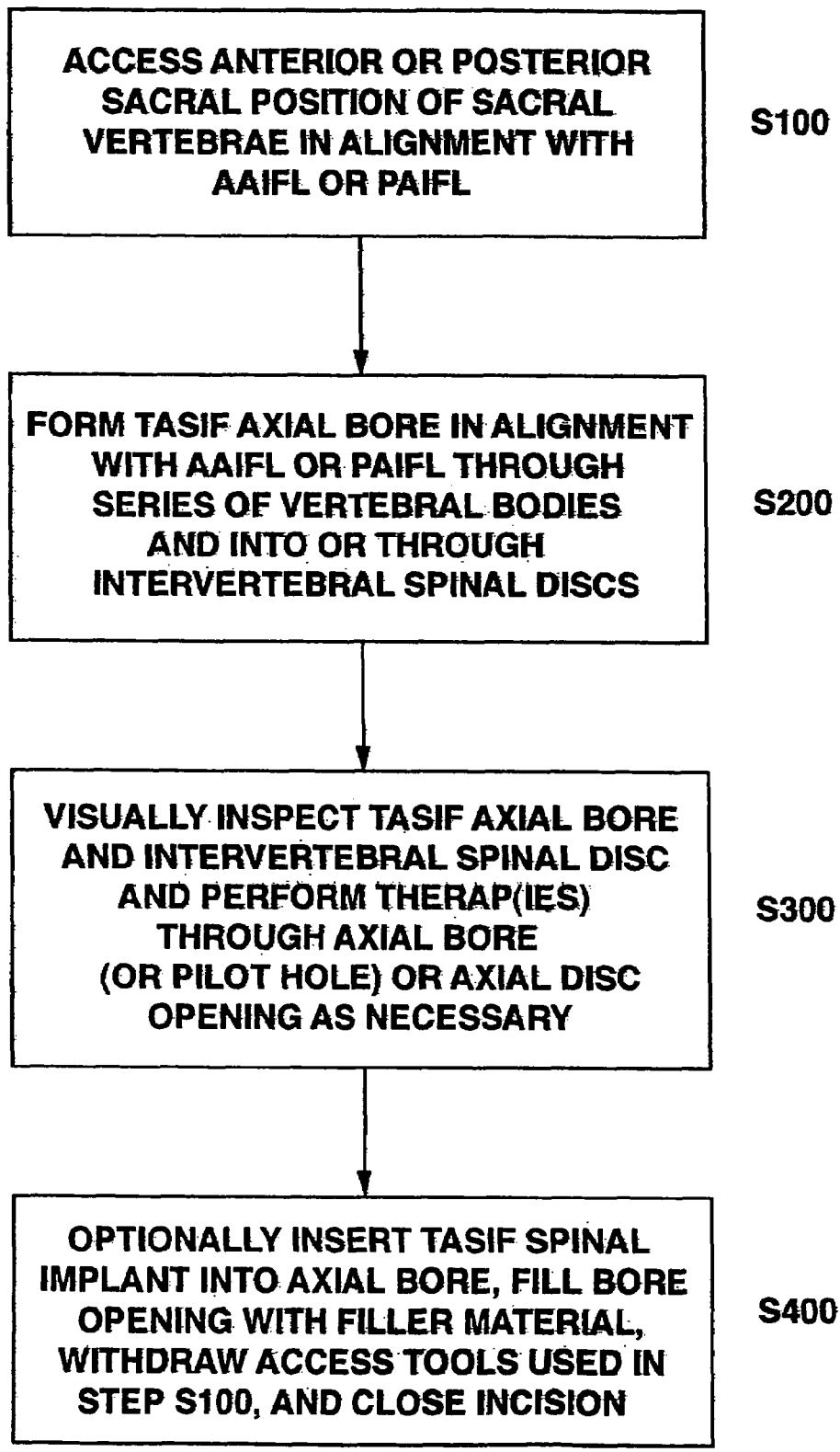
FIG. 6 is a simplified flow chart showing the principal surgical preparation steps of percutaneously accessing a posterior or anterior target point of the sacrum and forming a percutaneous tract following the visualized PAIFL or AAIFL of FIGS. 1-3, as well as subsequent steps of forming the TASIF bore(s) for treatment of accessed vertebral bodies and intervening discs and of implanting spinal implants therein.

The methods and surgical instrumentation and spinal implants disclosed in the above-referenced provisional application No. 60/182,748 and in co-pending, commonly assigned, patent application Ser. No. 09/640,222 filed Aug. 16, 2000, for METHOD AND APPARATUS FOR PROVIDING POSTERIOR OR ANTERIOR TRANS-SACRAL ACCESS TO SPINAL VERTEBRAE can be employed in the practice of the present invention. The '222 application discloses a number of related TASIF methods and surgical tool sets for providing posterior and anterior trans-sacral access to a series of adjacent vertebrae located within a human lumbar and sacral spine having an anterior aspect, a posterior aspect and an axial aspect, the vertebrae separated by intact or damaged spinal discs. Certain of the tools are selectively employed to form a percutaneous (i.e., through the skin) pathway from an anterior or posterior skin incision to a respective anterior or posterior position, e.g., a target point of a sacral surface or the cephalad end of a pilot hole bored through the sacrum and one or more lumbar vertebrae. The percutaneous pathway is generally axially aligned with the AAIFL or the PAIFL extending from the respective anterior or posterior target point through at least one sacral vertebral body and one or more lumbar vertebral body in the cephalad direction as visualized by radiographic or fluoroscopic equipment. The AAIFL and PAIFL follow the curvature of the vertebral bodies that they extend through in the cephalad direction.

Attention is first directed to the following description of FIGS. 1-6 is taken from the above-referenced parent provisional application No. 60/182,748. The acronyms TASF, AAFL, and PAFL used in the '748 application are changed to TASIF, AAIFL and PAIFL in this application to explicitly acknowledge that instruments can be introduced for inspection or treatments in addition to the fusion and fixation provided by spinal implants that may be inserted into the axial bores or pilot holes.

FIGS. 1-3 schematically illustrate the anterior and posterior TASIF surgical approaches in relation to the lumbar region of the spinal column, and FIGS. 4-5 illustrate the location of the TASIF implant or pair of TASIF implants within a corresponding posterior TASIF axial bore 22 or anterior TASIF axial bore 152 or pair of TASIF axial bores 22₁, 22₂ or 152₁, 152₂. Two TASIF axial bores and spinal implants or rods are shown in FIG. 5 to illustrate that a plurality, that is two or more, of the same may be formed and/or employed in side by side relation parallel with the AAIFL or PAIFL. Preferred TASIF surgical approaches for providing anterior and posterior trans-sacral access depicted in FIGS. 1-3 and preparing the TASIF axial bores 22 or 152 or $22_1$, $22_2$, or $152_1$, $152_2$ shown in FIGS. 4 and 5 are illustrated in further drawings. Preferred trans-sacral surgical access and TASIF pilot hole preparation tools are depicted in further drawings.

The lower regions of the spinal column comprising the coccyx, fused sacral vertebrae S1-S5 forming the sacrum, and the lumbar vertebrae L1-L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged spinal discs labeled D1-D5 in FIG. 1. FIGS. 2 and 3 depict the posterior and anterior view of the sacrum and coccyx.

The method and apparatus for forming an anterior or posterior TASIF axial bore initially involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies to be fused, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2.

It should be noted that the formation of the anterior tract 26 through presacral space under visualization described above is clinically feasible as evidenced by clinical techniques described by J. J. Trambert, MD, in "Percutaneous Interventions in the Presacral Space: CT-guided Precoccygeal Approach—Early Experience (*Radiology* 1999; 213:901-904).

FIG. 6 depicts, in general terms, the surgical steps of accessing the anterior or posterior sacral positions illustrated in FIGS. 1-3 (S100) forming posterior and anterior TASIF axial bores (S200), optionally inspecting the discs and vertebral bodies, performing disc removal, disc augmentation, and vertebral bone reinforcement (S300), and implanting posterior and anterior spinal implants and rods (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, an axial bore is bored from each point of penetration extending along either the PAIFL or AAIFL cephalad and axially through the vertebral bodies of the series of adjacent vertebrae and any intervertebral spinal discs (S200). The axial bore may be visually inspected using an endoscope to determine if the procedures of step S300 should be performed. Discoscopy or discectomy or disc augmentation of an intervening disc or discs or vertebroblasty of a vertebral body may be performed through the axial bore (S300). Finally, an elongated TASIF spinal implant or rod is inserted into each axial bore to extend cephalad and axially through the vertebral bodies of the series of adjacent vertebrae and any intervertebral spinal discs (S400). Other types of spinal implants for delivering therapies or alleviating pain as described above may be implanted in substitution for step S400.

Step S100 preferably involves creation an anterior or posterior percutaneous pathway that enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced as described in the above-referenced '222 application. An "anterior, presacral, percutaneous tract" extends through the "presacral space" anterior to the sacrum. The posterior percutaneous tract or the anterior, presacral, percutaneous tract is preferably used to bore one or more respective posterior or anterior TASIF bore in the cephalad direction through one or more lumbar vertebral bodies and intervening discs, if present. A single anterior or posterior TASIF bore is preferably aligned axially with the respective visualized AAIFL or PAIFL, and plural anterior or posterior TASIF bores are preferably aligned in parallel with the respective visualized AAIFL or PAIFL. Introduction of spinal implants and instruments for performing discectomies and/or disc and/or vertebral body augmentation is enabled by the provision of the percutaneous pathway and formation of the anterior or posterior TASIF bore(s).

It should be noted that performing step S100 in the anterior and/or posterior TASIF procedures may involve drilling a pilot hole, smaller in diameter than the TASIF axial bore, that tracks the AAIFL and/or PAIFL in order to complete the formation of the anterior and/or posterior percutaneous tracts. Step S300 may optionally be completed through the AAIFL/PAIFL pilot hole following step S100, rather than following the enlargement of the pilot hole to form the TASIF axial bore in step S200.

The preferred embodiments of the present invention involve methods and apparatus including surgical tool sets for forming pilot holes or curved, posterior and anterior, TASIF axial bores 22 or 152 or $22_1 \ldots 22_n$, or $152_1 \ldots 152_n$ shown in FIGS. 4 and 5 in axial alignment with the curved, visualized AAIFL and PAIFL. The surgical tool sets comprise elongated drill shaft assemblies supporting distal boring tools, e.g., mechanical rotating drill bits, burrs, augurs, abraders, or the like (collectively referred to as drill bits for convenience) that can be manipulated in use to straighten or form a selected curvature in a distal section or segment of each elongated drill shaft assembly. When the distal segment is straightened, the drill bit bores straight ahead to bore a relatively straight section of the TASIF axial bore. Then, when the distal segment is curved, the drill bit bores the next section of the TASIF axial bore at an angle to the previously drilled, more caudal section of the TASIF axial bore. The cumulative effect of boring alternate straight and curved sections results in an overall curvature in the TASIF axial bore that tracks the AAIFL or PAIFL as described above.

Figure 7:
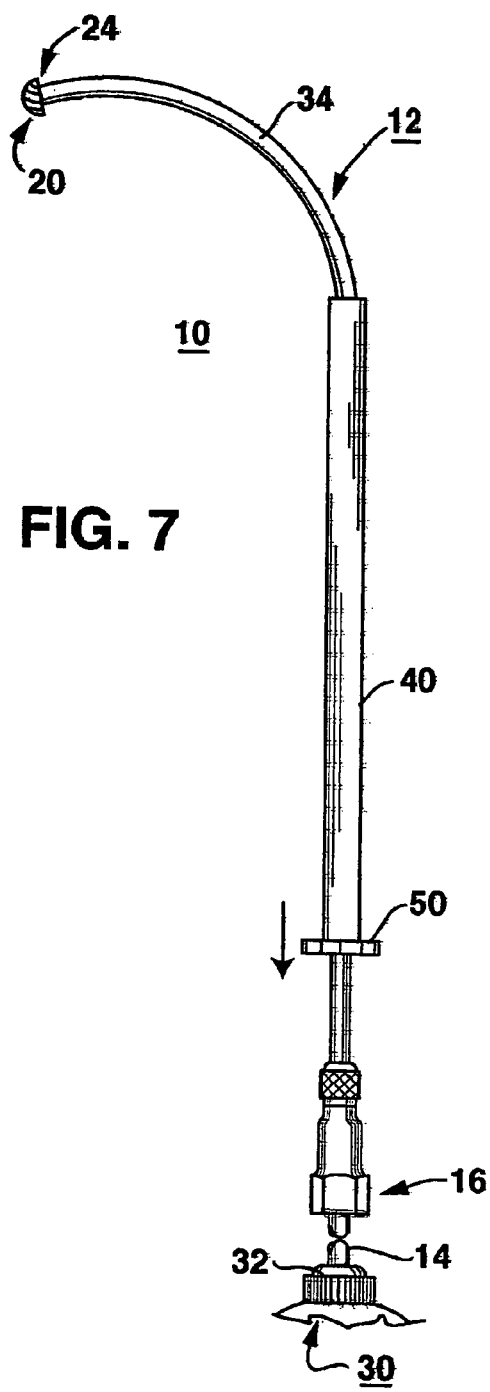
FIG. 7 is a plan view of one exemplary boring tool embodiment comprising an elongated drill shaft assembly and drill motor for forming a curved anterior or posterior TASIF axial bore, the drill bit having a 90° curve formed in the elongated drill drive shaft by retraction of an outer sheath.
Figure 8:
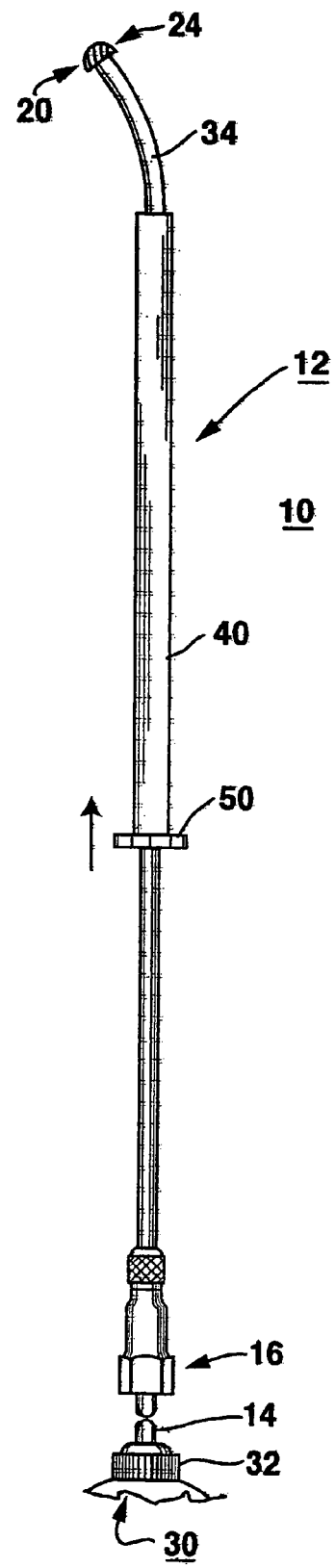
FIG. 8 is a plan view of the boring tool of FIG. 7 with a reduced curvature formed in the elongated drill shaft assembly by adjustment of the outer sheath.
Figure 9:
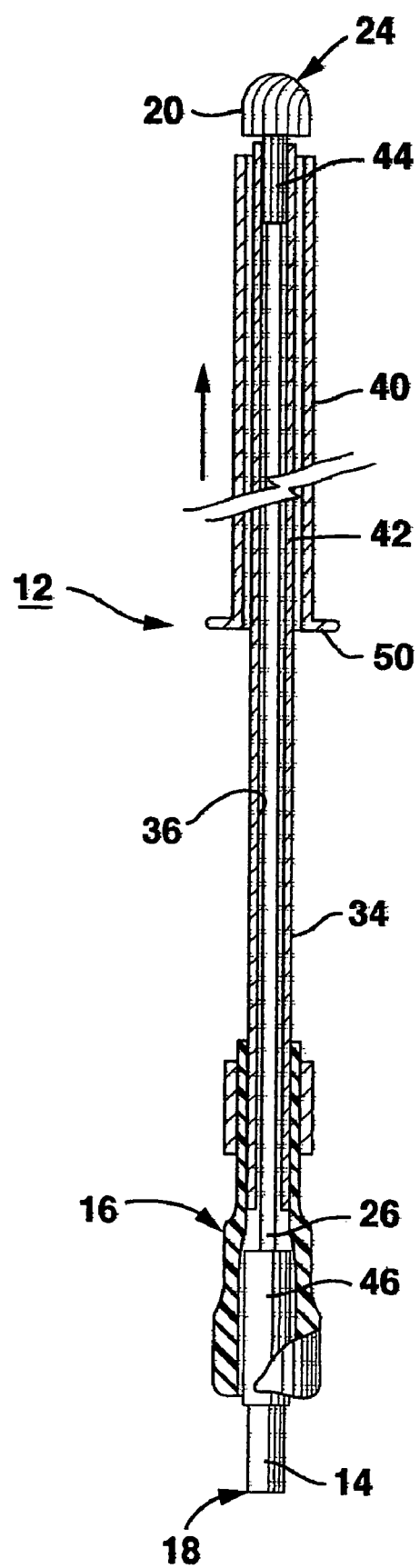
FIG. 9 is a cross-section view of the drill bit of FIGS. 7 and 8 with the curvature eliminated by full distal extension of the outer sheath to the distal end of the drill bit.

A First Exemplary Boring Tool:

FIGS. 7-9 show one exemplary boring tool 10 for boring a single one or a plurality of curved anterior or posterior TASIF axial bores aligned with the curved, visualized AAIFL or PAIFL as illustrated in FIGS. 10-18. The boring tool 10 comprises an elongated drill shaft assembly 12 and a drill motor 30 (shown in part) which may take any form. It will be understood that the drill motor 30 can be permanently attached to and form part of the proximal end of the elongated drill shaft assembly 12, but is depicted herein as a separate, detachable drill motor. The elongated drill shaft assembly 12 extends between an exposed proximal drive shaft end 14 at the proximal drill shaft assembly end 18 an exposed drill bit 20 at the distal drill shaft assembly end 24. The exposed proximal drive shaft end 14 is received within and attached to a chuck 32 of drill motor 30 in a manner well known in the art to rotate the drive shaft 26 extending from the drive shaft proximal end through the length of the elongated drill shaft assembly to the exposed distal drill bit 20. The exposed distal drill bit 20 may take any form of burr or auger or screw that can be rotated at a suitable speed to penetrate the dense and hard outer periostium and compact bone layers of the vertebral bodies and advance through the relatively softer, interiorly disposed, spongy bone. Then, the drill bit 20 is advanced in a curved path in the cephalad direction perforating each opposed face of each vertebral body and intervening disc while staying within the spongy bone of each vertebral body that is penetrated. The drill bit 20 is preferably radiopaque so that its advancement through vertebral bodies can be observed employing conventional imaging equipment.

The elongated drill shaft assembly 12 further comprises a pre-curved inner sheath 34 having an inner sheath lumen 36 receiving and enclosing the drive shaft 26, an outer sheath 40 having an outer sheath lumen 42 enclosing the inner sheath 34, and a housing 16 that is attached to the proximal end of the inner sheath 34. The outer sheath 40 can be retracted proximally over the inner sheath 34 so that a distal segment of the inner sheath 34 is exposed or extended distally over the inner sheath 34 so that the distal segment thereof is enclosed within the outer sheath lumen 42.

The drive shaft 26 is flexible and bendable and can formed of a single filament or multi-filar straight or coiled wire and is preferably radiopaque so that it can be observed using conventional imaging equipment. The distal end of the drive shaft 26 is attached to the drill bit 20 by in any manner, e.g., by welding to a proximal surface thereof or by being crimped inside a crimp tube lumen of a proximally extending crimp tube 44 of the drill bit 20 as shown in FIG. 9. The proximal end of the drive shaft 36 is received within a further crimp or weld tube 46 that extends distally from the proximal exposed drive shaft end 14 as shown in FIG. 9. The proximal exposed drive shaft end extends through a bearing in the proximal end wall of the housing 16 and is supported thereby for rotation by motor 30.

The outer diameters of the housing 16 and the drill bit 20 exceed the outer diameter of the straight outer sheath 40. The straight outer sheath 40 can be moved back and forth over the pre-curved inner sheath 34 between a proximal position depicted in FIG. 7, a distal position depicted in FIG. 9 and any number of intermediate positions bounded by the housing 16 and drill bit 20.

The straight outer sheath 40 is preferably formed of a stiff metal or plastic tube that is relatively stiffer and shorter in length than the more flexible, pre-curved inner sheath 34. The more flexible, pre-curved inner sheath 34 can be formed of a plastic or metal thin walled tubing and is pre-curved in a single plane to a suitable angle, e.g., about a 90° angle, in the distal segment thereof as shown in FIG. 7. The angle and radius of curvature of the distal segment can be selected along with the length and stiffness of the outer sheath 40 to meet the needs of tracking the AAIFL or the PAIFL. The stiffness of the outer sheath 40 is selected to enable it to be advanced distally to straighten the curvature of the distal segment of the inner sheath 34. However, the outer sheath 40 is flexible enough that it can be bent or curved within the confines of the curved TASIF axial bores as it is formed by the drill bit. In this way, the outer sheath can be advanced in the cephalad direction or retracted in the caudal direction and still conform to the curvature of the curved TASIF axial bore.

Posterior TASIF Axial Bore Formation:

FIGS. 10-13 show steps included in step S200 for forming a posterior TASIF axial bore 22 through sacral and lumbar vertebrae and intervening discs axially aligned with the visualized PAIFL of FIGS. 1 and 2 using the boring tool of FIGS. 7-9. The same steps can be employed to form a pilot hole of step S100 that can be enlarged in step S200. Using this technique to form the posterior TASIF axial bore, a small diameter bore forming tool (e.g. 3.0 mm diameter) is used to first bore a small diameter curved pilot hole following the imaginary, visualized PAIFL 20 through S1, L5 and L4. Then, the boring tool is removed, and a guidewire having a threaded distal screw-in tip is advanced through the pilot hole and screwed into to the caudal end of the pilot hole and into cephalad portion of the L4 body. An over-the-wire bore enlarging tool having a flexible body capable of tracking the curved guidewire is fitted over the proximal end of the guidewire and manually or mechanically rotated and advanced along it. In this way, the small pilot hole diameter is enlarged to form the anterior TASIF axial bore 22 having a diameter e.g. a 10.0 mm diameter, and the enlarging tool is then removed.

It will be understood that the illustrated diameter of the posterior TASIF axial bore hole 22 relative to sizes of the vertebral bodies is merely exemplary, and that it is contemplated that the pilot holes and bore hole diameters can range from range from about 1-10 mm and 3-30 mm, respectively. Moreover, it will be understood that a plurality of such posterior TASIF axial bores $22_1 \ldots 22_n$ can be formed in side by side relation generally aligned with the PAIFL.

Figure 10:
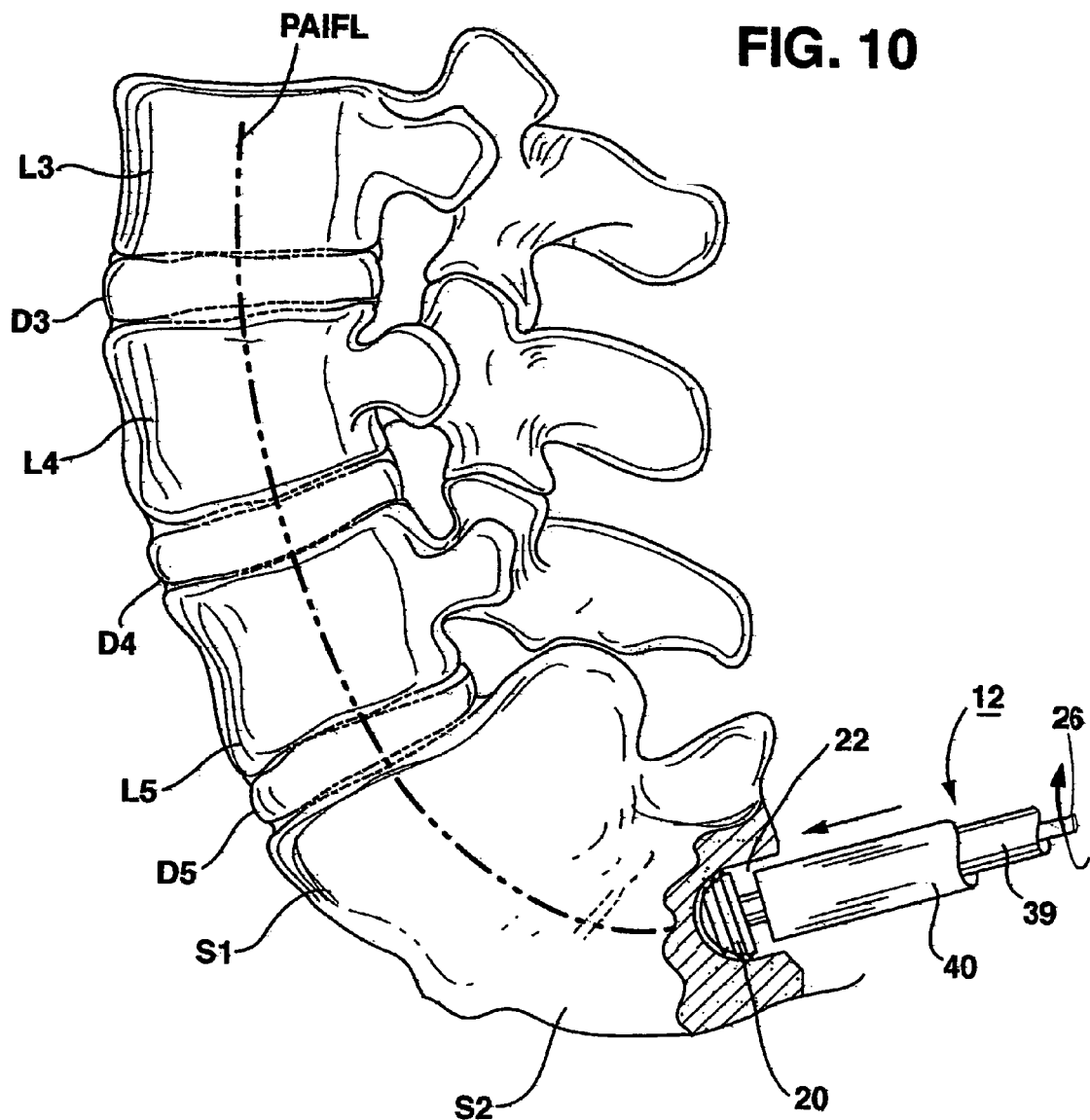
FIGS. 10-13 illustrate, in partial cross-section side views, one manner of forming a posterior TASIF axial bore through sacral and lumbar vertebrae and intervening discs axially aligned with the visualized PAIFL of FIGS. 1 and 2 using the boring tool of FIGS. 7-9.

In FIG. 10, the posterior surface of the sacrum is exposed in step S100 as described in the above-referenced '222 and '748 applications. The area of the patient's skin surrounding the incision site is surgically prepped, and the anus is excluded from the surgical field using adhesive drapes. The actual dermal entry site may be determined by the prone, preoperative CT scan or MRI study that maps the PAIFL. In step S100, an incision is made in the patient's skin over the posterior sacral surface of S2, and the subcutaneous tissue is separated to expose the posteriorly extending, bony ridge of the posterior sacral surface. A small laminectomy 14 is performed through the posterior ridge of the sacrum inferior. The thecal sac and nerve roots that are exposed by the laminectomy are gently retracted, and the terminal portion of the spinal canal is exposed.

The elongated drill shaft assembly 12 is axially aligned with the PAIFL at the posterior target point so that the initial penetration of the sacrum is substantially at right angles to the exposed sacral surface. A drill guide for receiving the drill drive shaft assembly for drilling or boring a TASIF axial bore from S2 along the visualized PAIFL 20 may optionally be attached to S2 and extended posteriorly through the exposed spinal canal and skin incision. In this starting position, the straight outer sheath 40 is fully distally extended to straighten the inner sheath 34, and the drill bit 20 is rotated to commence boring a posterior TASIF axial bore 22. The elongated drill shaft assembly 12 thus advances anteriorly to form a straight segment or section of the posterior TASIF axial bore 22.

Figure 11:
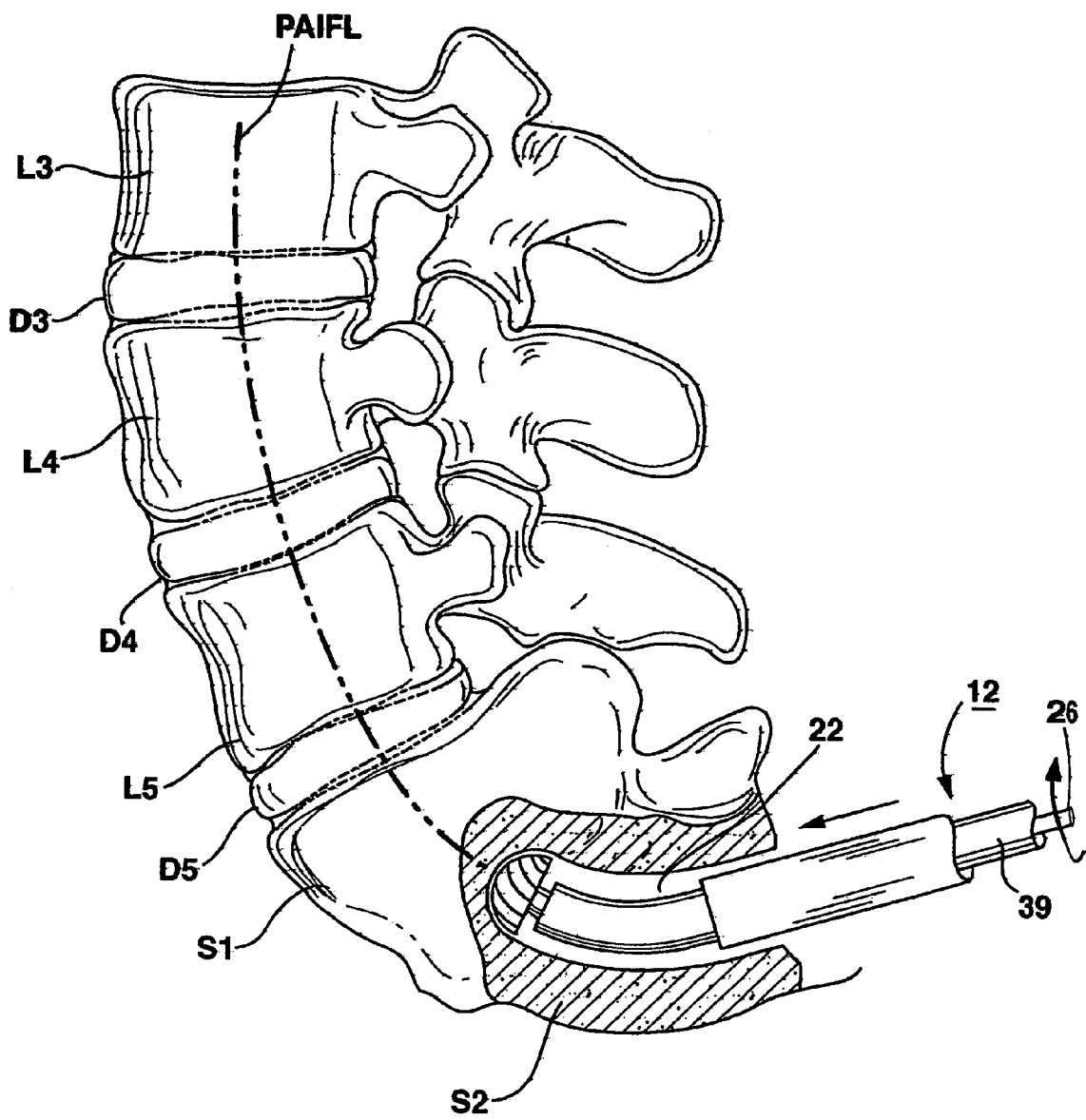
Figure 12:
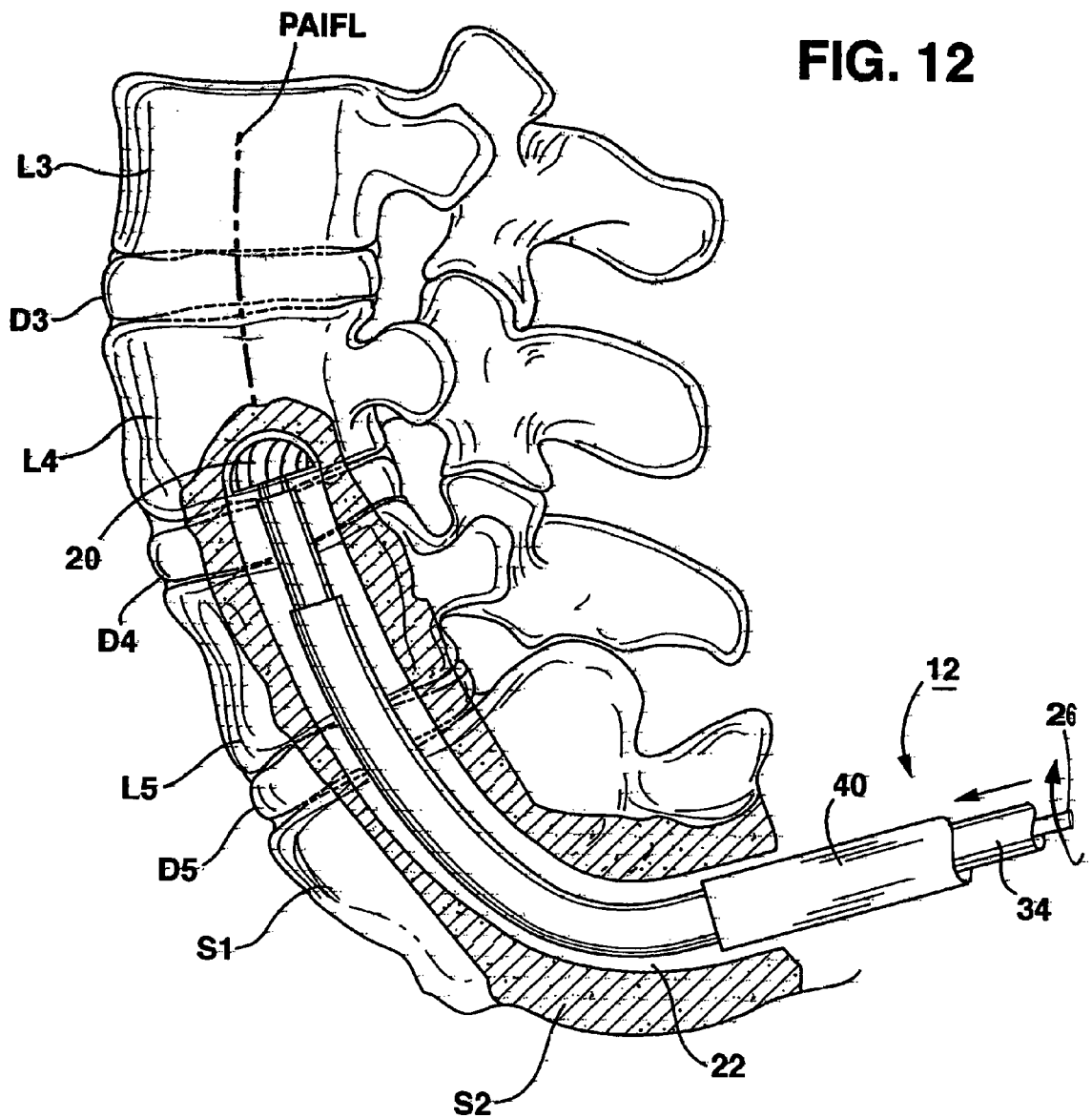
Figure 13:
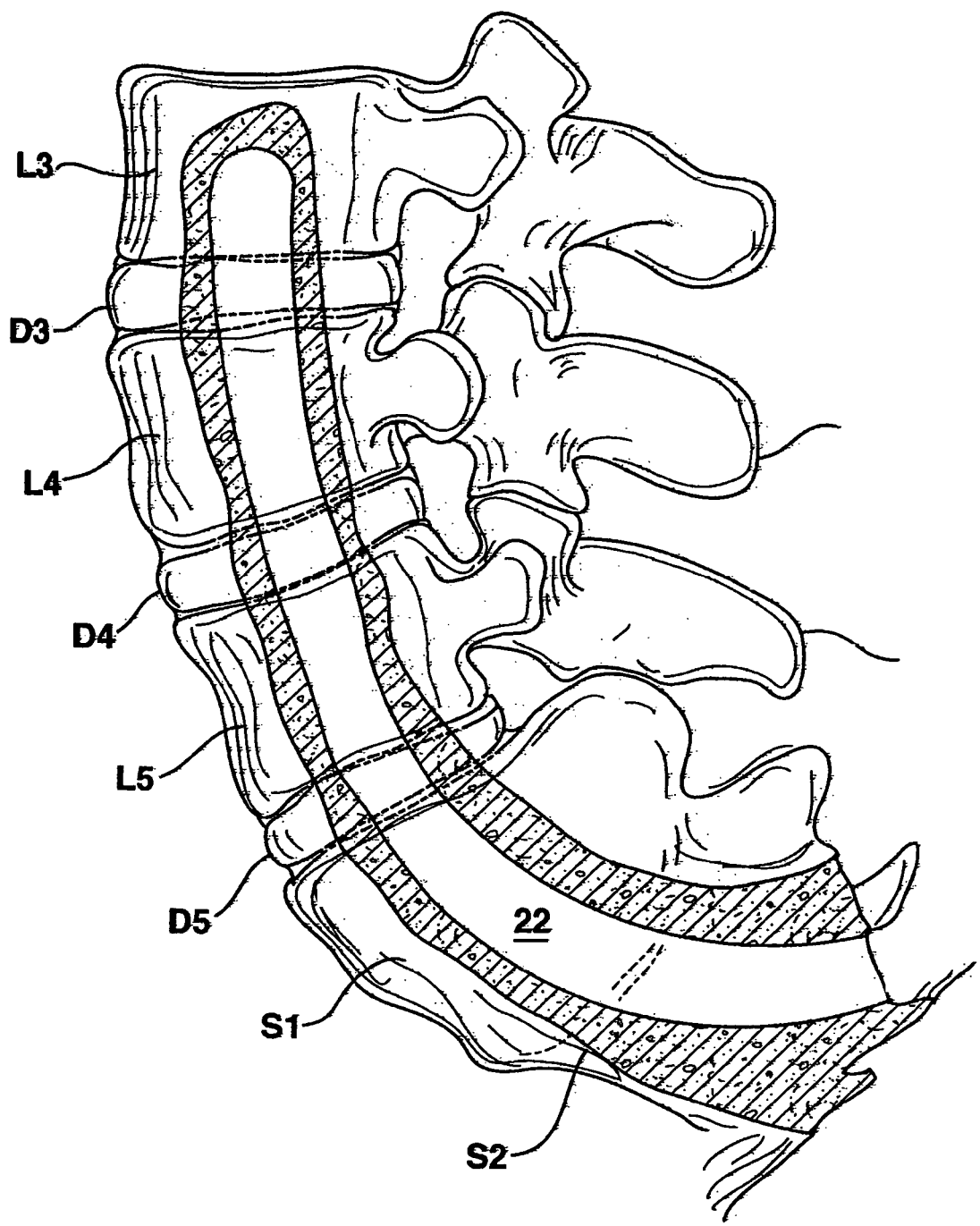

The progress of the drill bit 20 is observed using conventional imaging equipment. As the elongated drill shaft assembly 12 is extended anteriorly, it is necessary to retract the straight outer sheath 34 proximally to allow the inner sheath to curve in the cephalad direction to introduce a curvature in the cephalad segment of the posterior TASIF axial bore 22 as shown in FIG. 11. It is also necessary to orient and hold the proximal housing 16 so that the plane of curvature of the distal segment is aligned to the axis of the spine. The degree of curvature of the cephalad segment of the posterior TASIF axial bore 22 is continually adjusted by incremental proximal and distal movements of the straight outer sheath 40 at flange 50 to expose more or less of the distal segment of the curved inner sheath 34 as shown in FIG. 12. In this way, the drill bit 20 advances through the sacral vertebrae in the cephalad direction and toward the lumbar vertebral bodies while staying within the spongy bone of each vertebral body. Theoretically, any number of vertebral bodies of the spine can be bored through in the cephalad direction.

Figure 14:
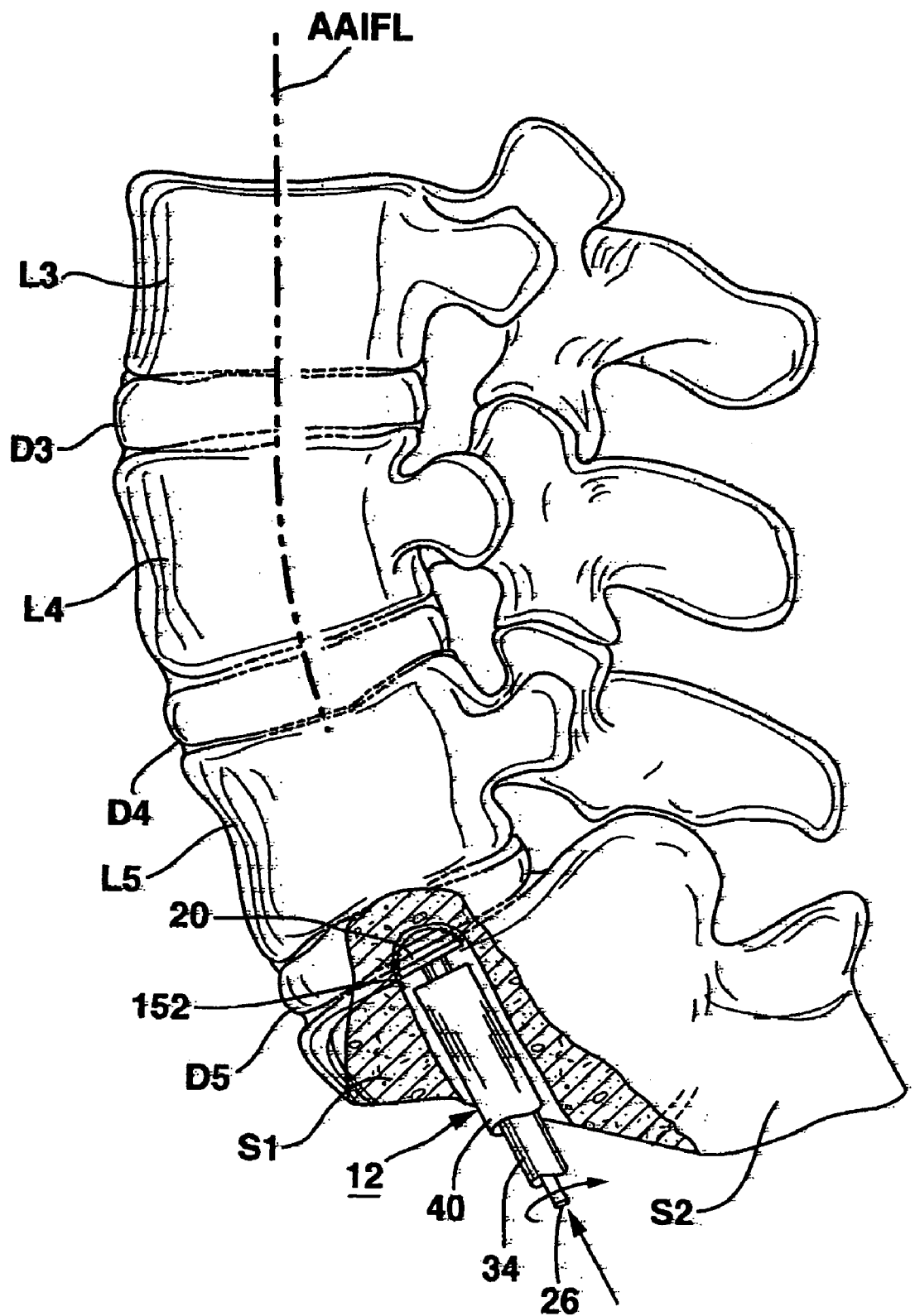
FIGS. 14-18 illustrate, in partial cross-section side views, one manner of forming an anterior TASIF axial bore through sacral and lumbar vertebrae and intervening discs axially aligned with the visualized AAIFL of FIGS. 1 and 2 using the boring tool of FIGS. 7-9.
Figure 15:
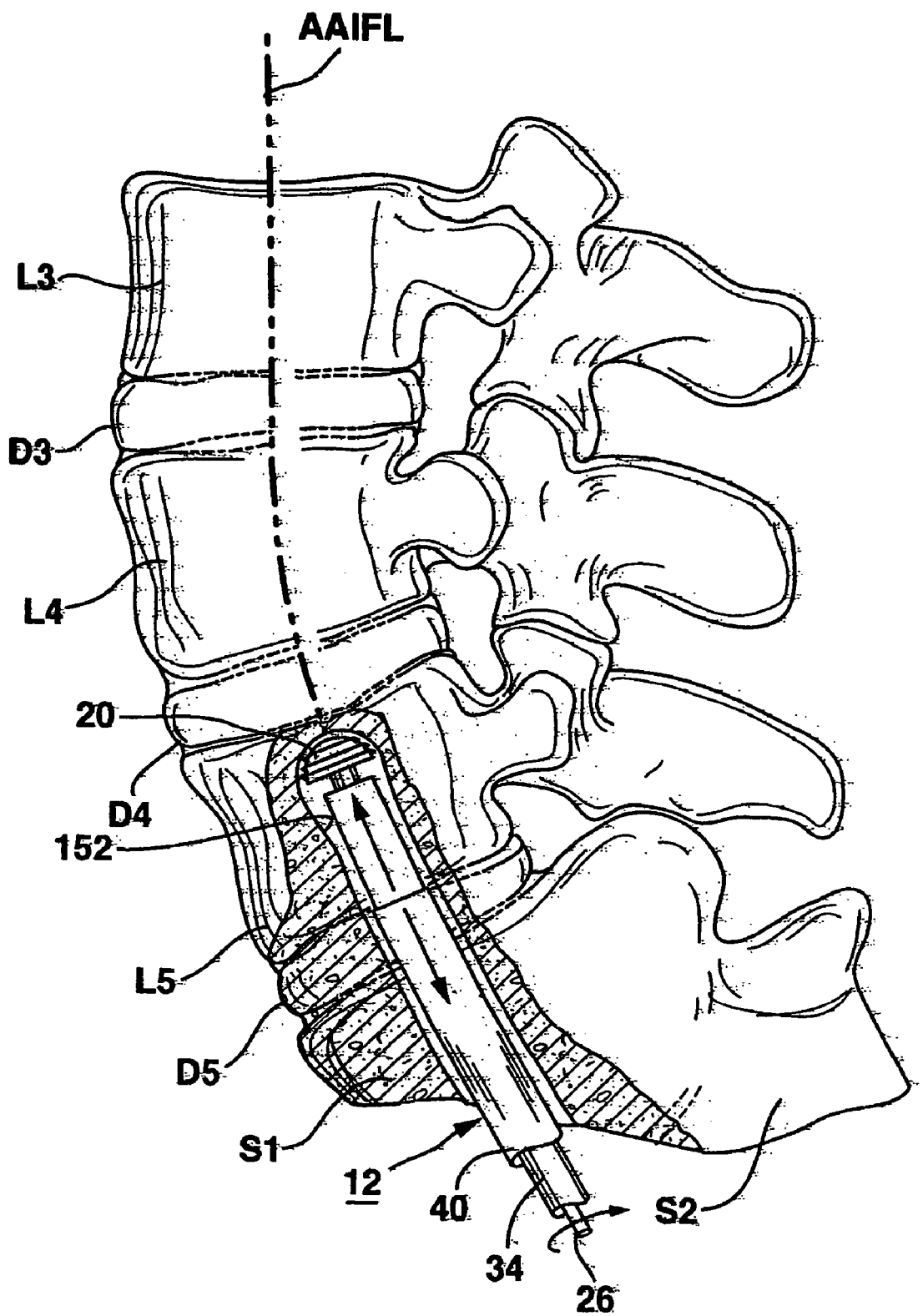
Figure 16:
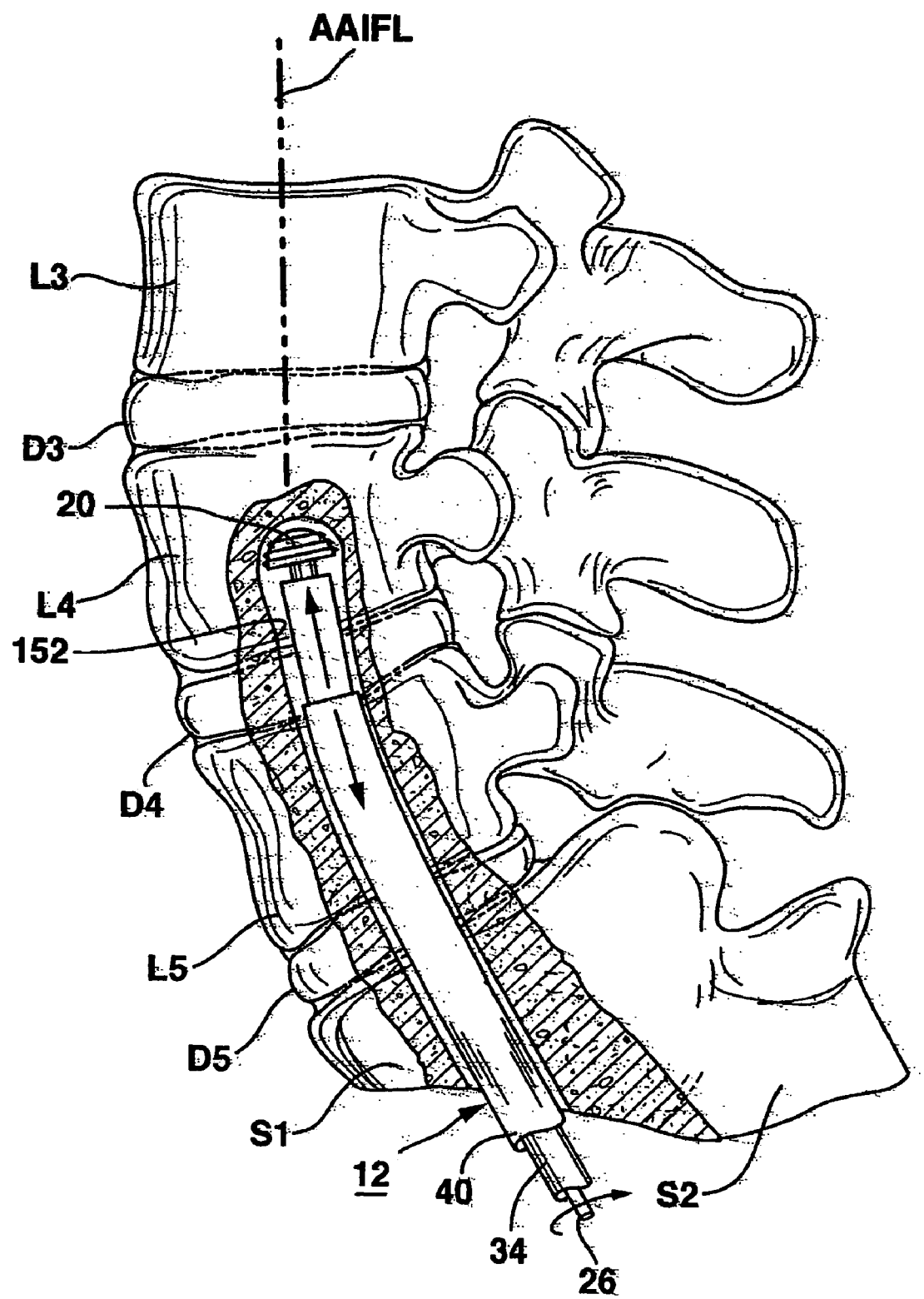

Anterior TASIF Axial Bore Formation:

FIGS. 14-16 show steps included in step S200 for forming an anterior TASIF axial bore 152 through sacral and lumbar vertebrae and intervening discs axially aligned with the visualized AAIFL of FIGS. 1 and 2 using the boring tool of FIGS. 7-9. The same steps can be employed to form a pilot hole of step S100 that can be enlarged in step S200. It will be understood that the illustrated diameter of the anterior TASIF axial bore hole 152 relative to sizes of the vertebral bodies is merely exemplary, and that it is contemplated that the pilot holes and bore hole diameters can range from about 1-10 mm and 3-30 mm, respectively. Moreover, it will be understood that a plurality of such anterior TASIF axial bores $152_1 \ldots 152_n$ can be formed in side by side relation generally aligned with the AAIFL.

In FIG. 14, the elongated drill shaft assembly 12 is axially aligned with the AAIFL at the anterior target point so that the initial penetration of the sacrum is substantially at right angles to the opposed faces of S1 and L5 cephalad to the sacral surface of penetration. This anterior sacral surface starting point is accessed in step S100 from an incision in the patient's skin alongside the coccyx and via a percutaneous tract formed in the pre-sacral space which may or may not include a tract forming structure or tool as disclosed in the above-referenced '222 and '748 applications.

In this starting position, the straight outer sheath 40 is either fully distally extended to straighten the inner sheath 34 or retracted slightly depending on the patient's anatomy to provide an optimal orientation to the AAIFL. The drill bit 20 is rotated to commence boring an anterior TASIF axial bore 152, and the elongated drill shaft assembly 12 advances anteriorly to form a relatively straight or slightly curved segment of the posterior TASIF axial bore 22.

Again, the progress of the drill bit 20 is observed using conventional imaging equipment. As the elongated drill shaft assembly 12 is extended in the cephalad direction through S1, D5 (if present) and L5, it becomes necessary to retract the straight outer sheath 34 proximally to allow the inner sheath to curve in the cephalad direction to introduce a greater degree of curvature in the cephalad segment of the anterior TASIF axial bore 152 as shown in FIG. 15. Again, it is also necessary to orient and hold the proximal housing 16 so that the plane of curvature of the distal segment is aligned to the axis of the spine. This could be accomplished using external reference markings on the proximal housing 16. The degree of curvature of the cephalad segment of the anterior TASIF axial bore 152 is continually adjusted by incremental proximal and distal movements of the straight outer sheath 40 at flange 50 to expose more or less of the distal segment of the curved inner sheath 34 as shown in FIG. 15. In this way, the drill bit 20 advances through the sacral vertebrae in the cephalad direction and through the lumbar vertebral bodies while staying within the spongy bone of each vertebral body.

Figure 17:
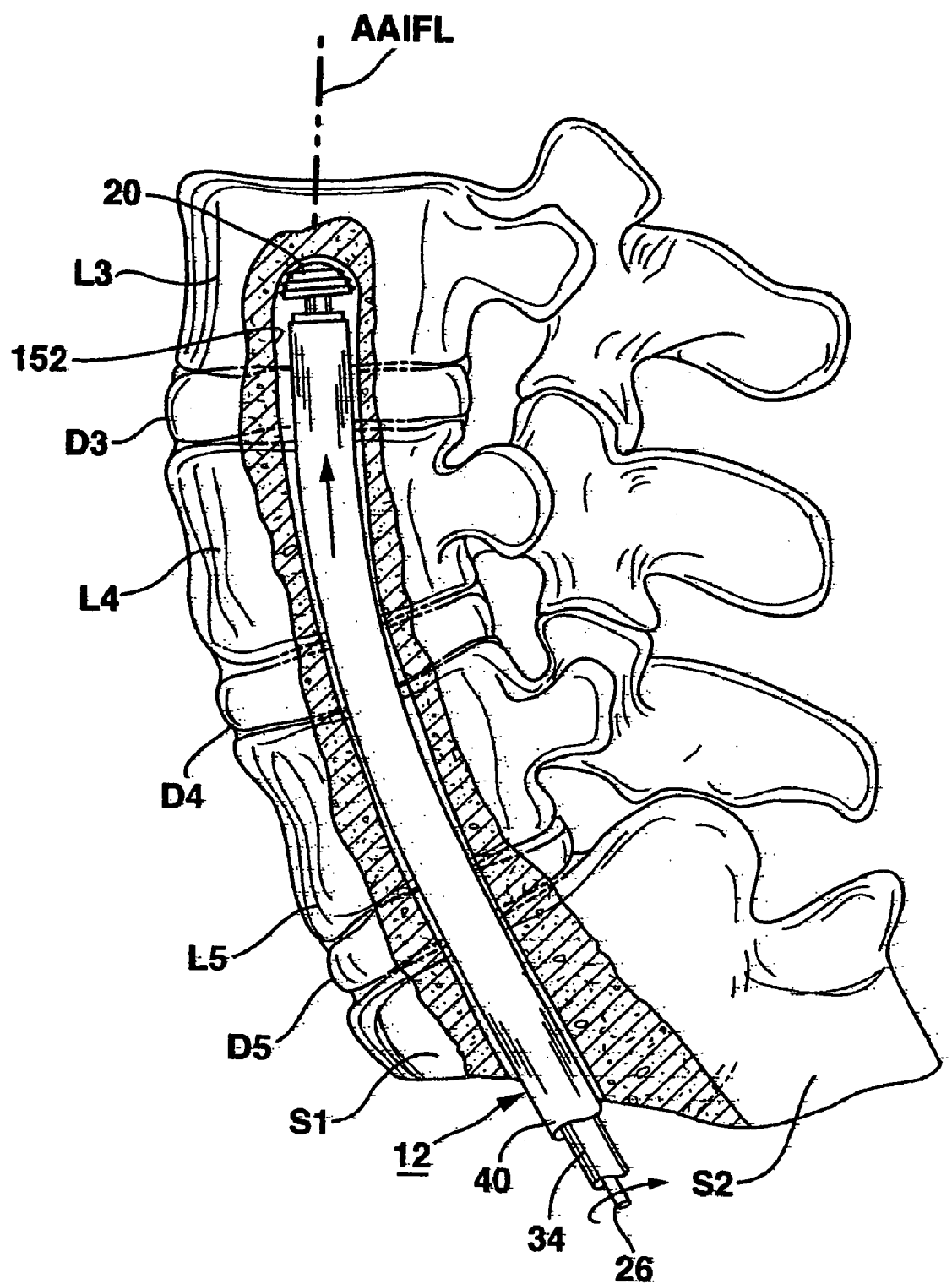
Figure 18:
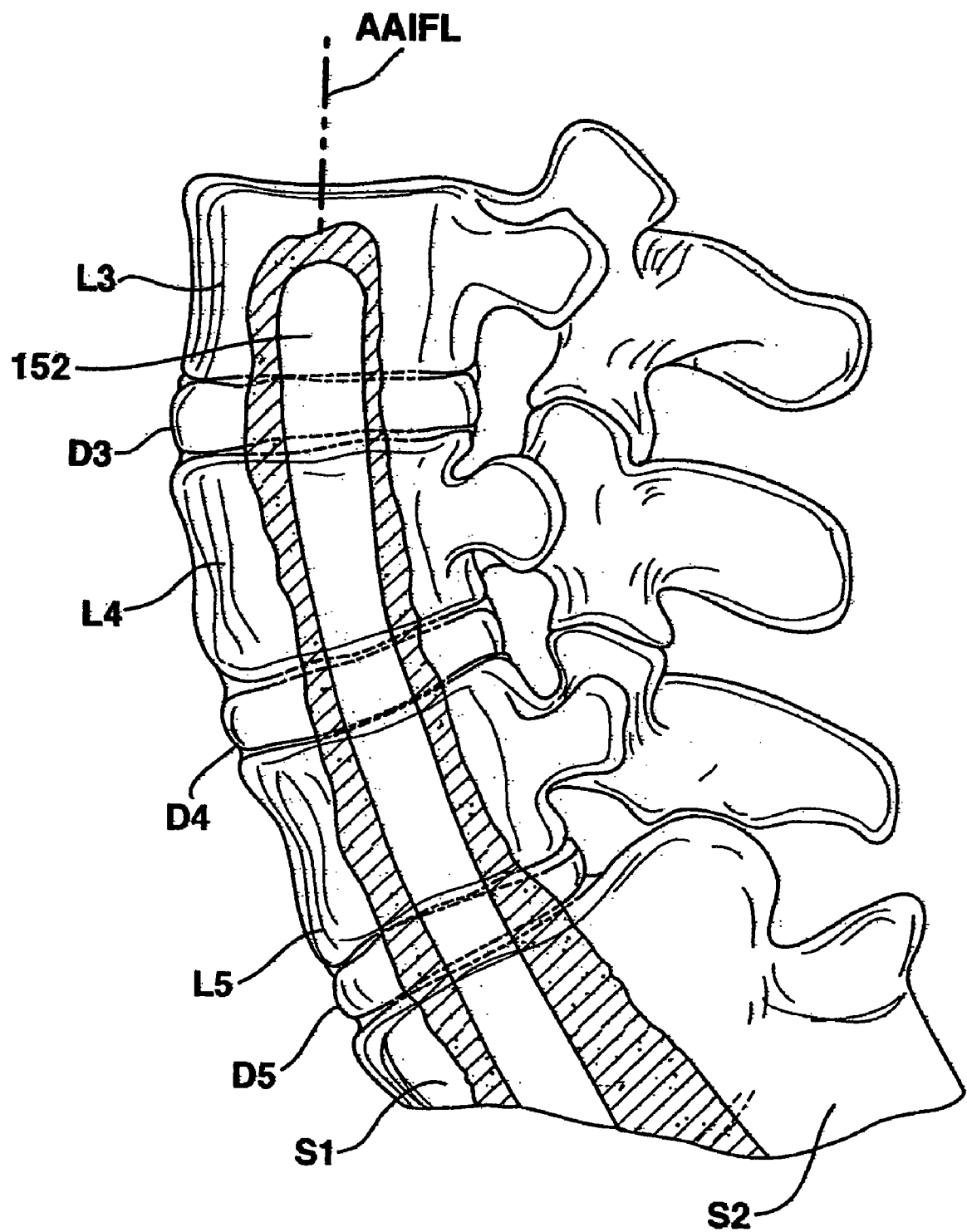

Slight but abrupt angular changes in the overall curvature of the anterior TASIF axial bore 152 are made within the vertebral bodies of L5 and L4 as shown in FIGS. 15 and 16, by caudal retraction of the outer sheath 40 and cephalad advancement of inner sheath 34. It is expected that it will usually be easier to adjust the angle of the drill bit 20 within the spongy bone interior to the vertebral bodies than in the disc space or while boring through the harder exterior vertebral bone. Therefore, after the spongy interior bone is bored through, the outer sheath 40 is advanced in the distal direction to straighten the angle of advancement of the drill bit 20 through the harder vertebral bone on either side of the disc. This straightened boring angle of attack is shown in FIG. 17, for example, where the drill bit 20 is advanced across the opposed faces of vertebral bodies L4 and L5 with the outer sheath 40 fully advanced in the cephalad direction. This process results in short relatively straight sections separated by more curved sections of the of the anterior TASIF axial bore 152. Thus, the resulting anterior TASIF axial bore 152 shown in FIG. 18 exhibits an overall curvature tracking the spinal curvature and the visualized AAIFL, but the curve radius varies, showing a shorter radius within the central portions of vertebral bodies L5 and L4.

A Further Exemplary Boring Tool

FIGS. 19-21 illustrate a further embodiment of an exemplary boring tool 110 comprising a drill motor 30 and an elongated drill shaft assembly 112 employing one or more tip deflection wire 104 (FIG. 21) for imparting a desired curvature in the distal segment of sheath 134. The sheath 134 extends from the distal end 124 into the housing 124 in the manner of sheath 34 depicted in FIG. 9, but it encloses an inner lumen 136 for receiving the drive shaft 126 and a radially offset tip deflection wire lumen 102 receiving a tip deflection wire 104. The distal end of the drive shaft 126 is attached to the drill bit 120 in the manner described above for attachment of the distal end of drive shaft 26 with the drill bit 20. The proximal end of the drive shaft 126 is attached to the proximal exposed drive shaft end 114 in the manner that the proximal end of the drive shaft 26 is attached to the proximal exposed drive shaft end 14. The drive shaft 126 may take any form including the depicted coiled wire form with or without a core wire extending through the coiled wire lumen.

The tip deflection wire 104 extends through the wire lumen extending along one side of the drive shaft sheath 134 between an attachment point at the distal end 124 and an attachment within housing 138 with distal segment curvature control ring 106 mounted on housing 138. The distal segment of drive shaft sheath 134 distal to junction 136 is more flexible than the proximal segment of drive shaft sheath 134 proximal to junction 136. The distal segment curvature control ring 106 is located over the cylindrical surface of housing 138, and an inwardly extending member extends into an elongated groove 108 in the housing 138 where it is attached to the proximal end of the tip deflection wire 104. The retraction of tip deflection wire 104 to form the curves in the drive shaft distal segment depicted in FIGS. 19 and 20 is effected by sliding the control ring 106 proximally from a rest or neutral position wherein the distal segment assumes a straight distal segment shape 134' as depicted in broken lines in FIG. 19. It will be understood that the length of the distal segment of the drive shaft 126 and the range of motion of the control ring 106 from the neutral position can be selected so as to form any angle or range of curvature that may be found desirable. Furthermore, it will be understood that the range of motion of the control ring 106 from the neutral position can be selected such that the control ring may be pushed distally from the neutral position to impart a curvature in the distal segment that is opposite to the curvatures depicted in FIGS. 19 and 20. The tip deflection wire 104 can therefore be either a pull wire for retraction only or a push-pull wire for retraction and extension.

The boring tool 110 can be employed to form the posterior and anterior TASIF axial bores 22 and 152 or a plurality of the same in the same manner as described above with respect to FIGS. 10-18. The curvature of the posterior and anterior TASIF axial bores 22 and 152 is controlled by manipulation of the distal segment curvature control ring 106 as the drill bit 120 is advanced in the cephalad direction from the starting points depicted in FIGS. 10 and 14.

A Still Further Exemplary Boring Tool:

FIGS. 22-25 illustrate a further embodiment of an exemplary boring tool 210 comprising a drill motor 230 and an elongated drill shaft assembly 212. The elongated drill shaft assembly 212 further comprises a straight inner sheath 234 having an inner sheath lumen 236 receiving and enclosing the drive shaft 226, a straight outer sheath 240 having an outer sheath lumen 242 enclosing the inner sheath 234, and a housing 238 that is attached to the proximal end of the inner sheath 234. In this embodiment, the inner sheath 234 is optional and can be eliminated to reduce the overall diameter of the elongated drill shaft assembly 212.

The drive shaft 226 is flexible and bendable enough to be either be straight when extended distally or curved in use as described below and can formed of a single filament or multifilar straight or coiled wire that is preferably radiopaque so that it can be observed using conventional imaging equipment. The distal end of the drive shaft 226 is attached to the spherical drill bit 220 by in any manner, e.g., by welding to a proximal surface thereof or by being crimped inside a crimp tube lumen of a proximally extending crimp tube 244 of the drill bit 220 as shown in FIG. 23. The proximal end of the drive shaft 236 is received within a further crimp or weld tube 246 that extends distally from the proximal exposed drive shaft end 214 as shown in FIG. 23. The proximal exposed drive shaft end 214 extends through a bearing in the proximal end wall of the housing 238 and is supported thereby for rotation by motor 30.

The flexible outer sheath 240 is generally circular in cross-section and extends between a push-pull proximal handle 250 and a distal end thereof. The outer sheath lumen 242 is radially offset from the axis of the flexible outer sheath 240 so that the drill shaft 226 and optional inner sheath 234 extend through the outer sheath lumen to locate the drill bit 220 offset from the axis of the flexible outer sheath 240 as shown in FIGS. 23 and 24. A sleeve-shaped, thrust bearing 228 formed of a hard plastic or metal material is disposed in the outer sheath distal end surrounding the distal end opening of the outer sheath lumen 242 and projecting slightly distally therefrom. The remaining exposed portion of the outer sheath 240 is flexible and compressible to be advanced through a bore hole formed by the drill bit 220. The outer diameters of the housing 238 and the drill bit 220 exceed the outer diameter of the flexible outer sheath 240. The flexible outer sheath 240 can be moved back and forth over the inner sheath 234 between a proximal position depicted in FIG. 22 and a distal position depicted in FIG. 25. The outer diameter of the drill bit 220 is approximately equal to or slightly larger than the outer diameter of the outer sheath 240 as shown in FIGS. 23 and 24.

A curvature in the distal segment of the outer and inner sheaths 240 and 234 toward the radial offset direction D (FIG. 23) is formed when the outer sheath 240 is advanced distally to its full extent as shown in FIG. 25. The distal surface of the thrust bearing 228 bears against the proximal spherical surface of the drill bit 220 when force is applied by pushing the outer sheath 240 distally at handle 250 and/or pulling the inner sheath 234 proximally at housing 238. The axial offset of the outer sheath lumen 242 and the flexibility of the outer sheath 240 just proximally to thrust bearing 228 cooperate to laterally deflect the drill bit 220 toward the radial offset direction D. The thinner wall of the outer sheath 240 in the radial offset direction contributes to its axial compression and inducement of the depicted curvature. It will be understood that the angular deflection of the drill tip 220 and the range of curvature of the distal segment of the outer and inner sheaths 240 and 234 toward the radial offset direction D can be selected by the selection of materials and the offset of the outer sheath lumen 242 from the axis of outer sheath 240.

The boring tool 210 can be employed to form the posterior and anterior TASIF axial bores 22 and 152 or a plurality of the same in the same manner as described above with respect to FIGS. 10-18. The curvature of each section of the posterior and anterior TASIF axial bores 22 and 152 is controlled by proximal and distal manipulation of the outer sheath 240 with respect to inner sheath 234 as the drill bit 220 is advanced in the cephalad direction from the starting points depicted in FIGS. 10 and 14.

It will be understood that the above-described embodiments of TASIF axial bore or pilot hole boring tools can be modified in many ways. For example, the elongated drive shaft assemblies can be modified to provide fluid lumens for pumping flushing fluids into the TASIF axial bores at the distal ends thereof and for conveying flushing fluid and bone fragments proximally to the exterior of the patient's body. Also, the elongated drive shaft assemblies can be modified to provide a guide wire lumen extending from the proximal to the distal ends thereof for advancement over a guidewire. Suitable drive motors for rotating a drive shaft over a guidewire and drive shaft assemblies having flushing capabilities are disclosed in U.S. Pat. No. 6,066,152, for example.

When a single posterior or anterior TASIF axial bore 22 or 152 is formed, it can be formed in axial or parallel alignment with the visualized axial AAIFL and PAIFL as described. Similarly, multiple posterior or anterior TASIF axial bores can be formed all in parallel alignment with the visualized axial AAIFL and PAIFL or with at least one such TASIF axial bore formed in axial alignment with the visualized axial AAIFL and PAIFL.

Diverging TASIF Axial Bores:

Moreover, multiple anterior or posterior TASIF axial bores can be formed all commencing at an anterior or posterior target point of FIGS. 1-3 and extending in the cephalad direction with each TASIF axial bore diverging apart from the other and away from the visualized axial AAIFL and PAIFL. The diverging TASIF axial bores terminate as spaced apart locations in a cephalad vertebral body or in separate cephalad vertebral bodies.

Figure 26:
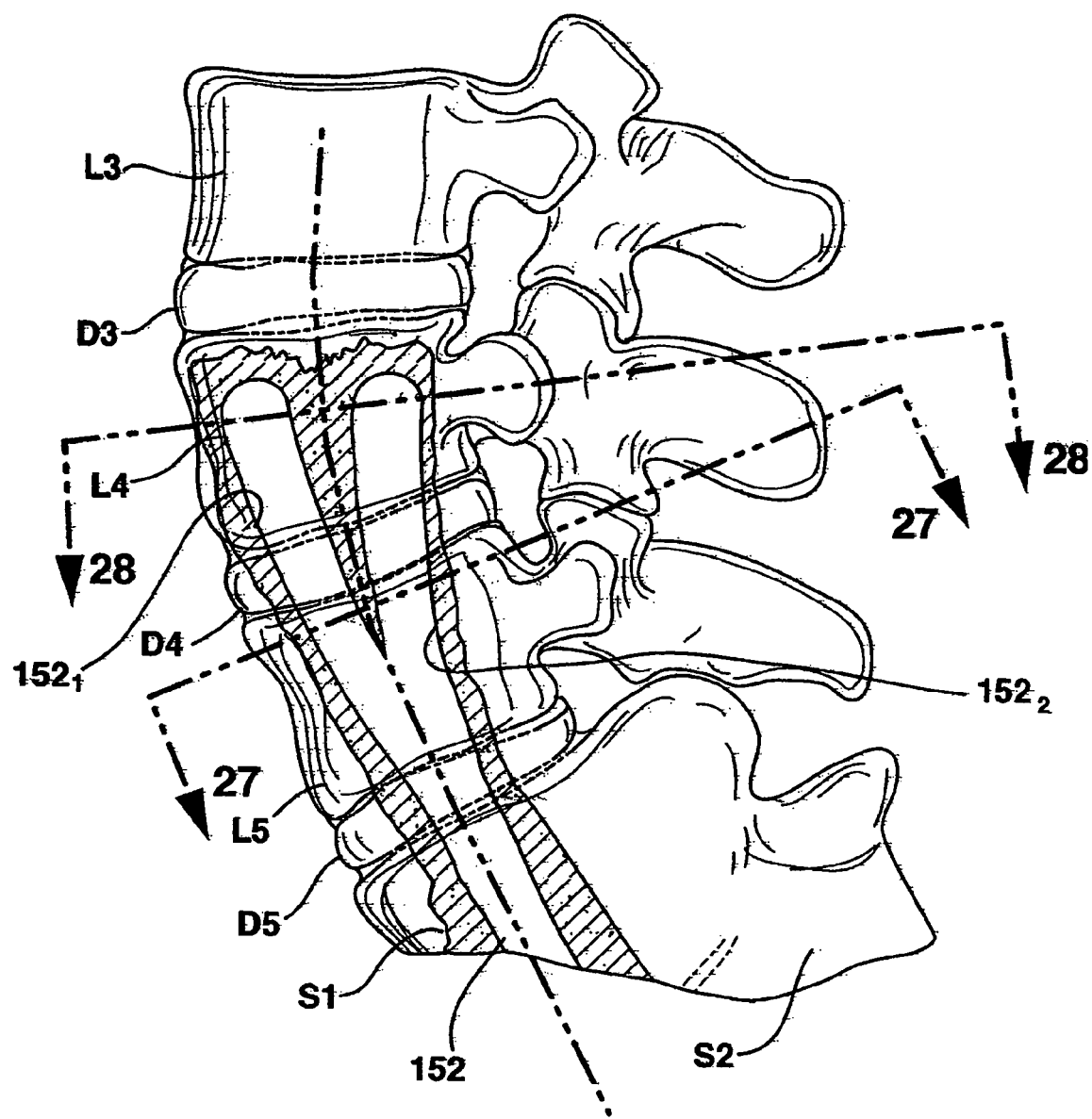
FIG. 26 depicts, in a partial cross-section side view, the formation of a plurality of curved TASIF axial bores that diverge apart from a common caudal section in the cephalad direction.
Figure 27:
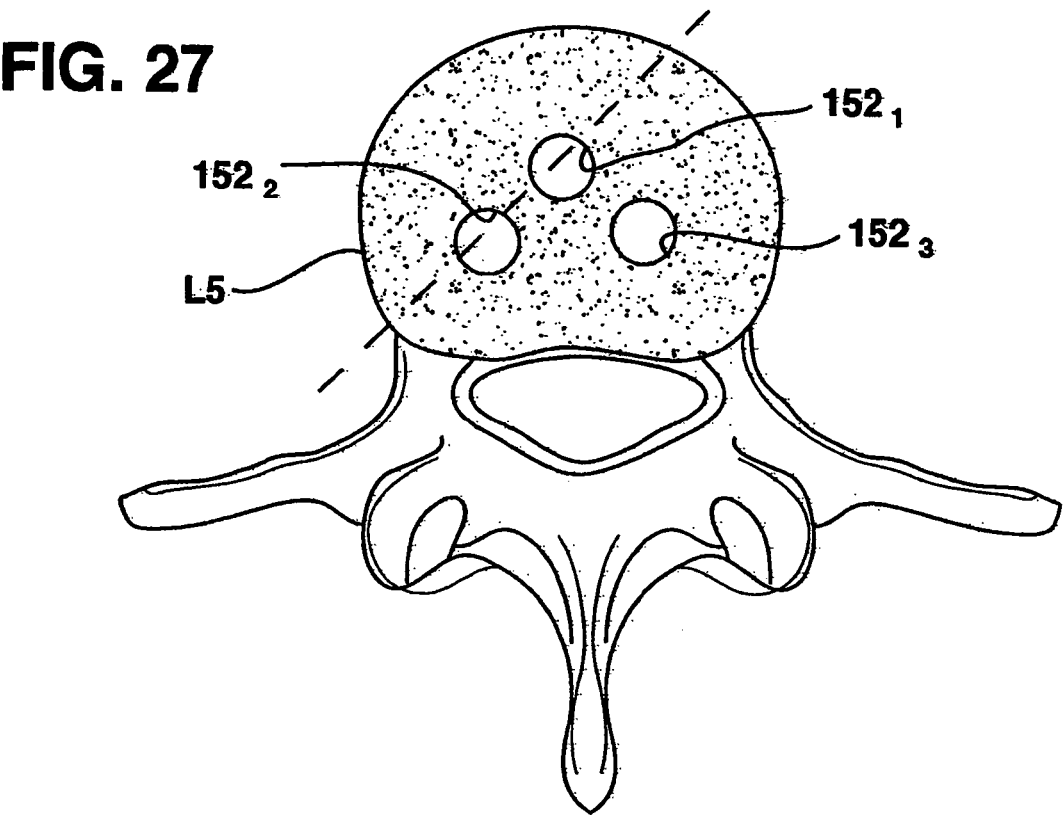
FIGS. 27 and 28 depict, in partial cross-section end views taken along lines 27-27 and 28-28, respectively, of FIG. 26, the divergence of the plurality of curved TASIF axial bores.
Figure 28:
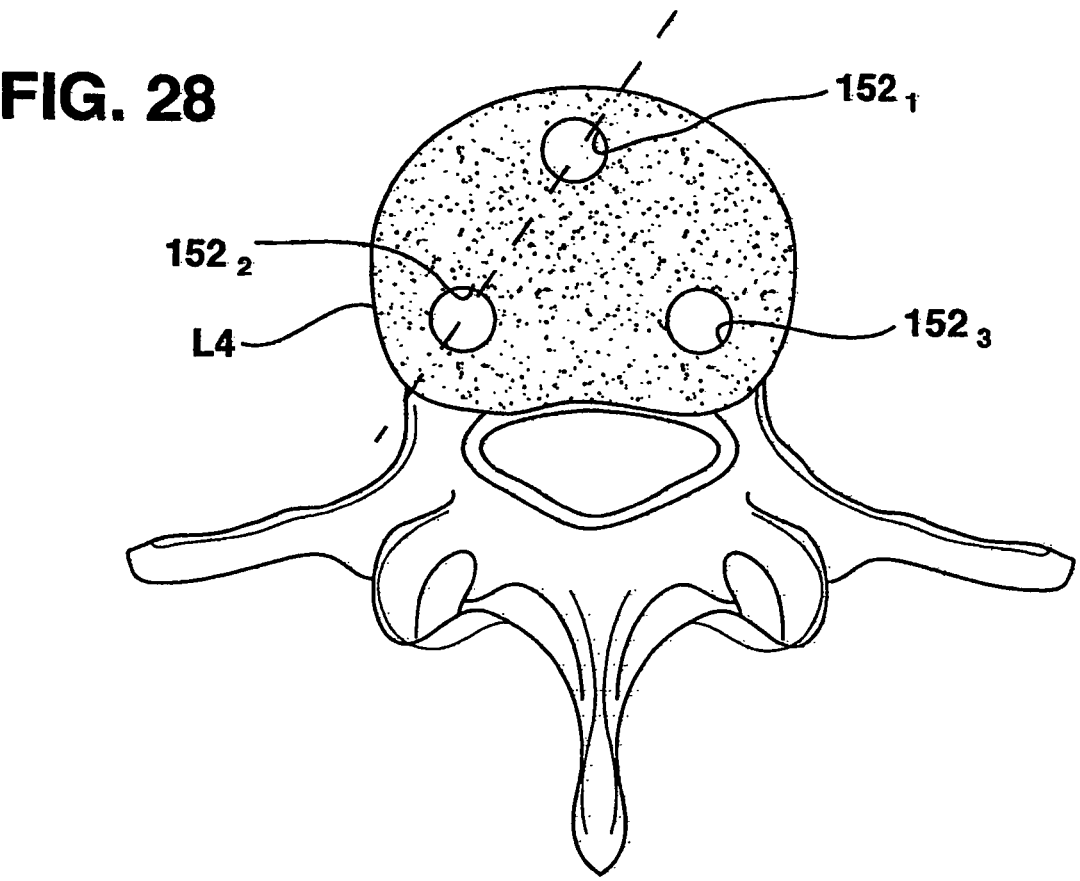

For example, FIGS. 25-27 depict a group of three anterior TASIF axial bores $152_1$, $152_2$, $152_3$ that are bored from a common caudal entrance bore section 152' starting at the anterior target point and extending in the cephalad direction generally following the curvature of the AAIFL but diverging outwardly the divergence from the common entry bore section can start in the sacral vertebra or in L5 or in L4 or in any other cephalad vertebra that the bore extends into or through. A "tripod" of the diverging TASIF axial bores $152_1$, $152_2$, $152_3$ is formed as shown in FIGS. 26 and 27. The common caudal entrance bore section 152' through S1, and traversing disc D5 and part of L4 can be larger in diameter than the diverging TASIF axial bores $152_1$, $152_2$, $152_3$ to accommodate the insertion of three elongated spinal implants therein. It is believed that the insertion of elongated spinal implants within the "tripod" of the diverging TASIF axial bores $152_1$, $152_2$, $152_3$ can substantially strengthen and enhance fusion of L4, L5 and S1. The diverging TASIF axial bores $152_1$, $152_2$, $152_3$ can be extended further than shown in FIGS. 25-27.

Counterbored Recesses for Anchoring Spinal Implants:

Thus, the above-described tool sets can be employed to bore a curved trans-sacral axial bore or pilot hole in alignment with said axial fusion line cephalad and axially through the vertebral bodies of said series of adjacent vertebrae and any intervertebral spinal discs. The alignment can be axial alignment as shown in FIG. 4, or parallel as shown in FIG. 5 or diverging alignment as shown in FIGS. 25-27. The above described tool sets can also be employed to form relatively straight trans-sacral axial bores through a sacral vertebra and at least one cephalad lumbar vertebra. Recesses are formed in the relatively straight or curved trans-sacral bores in a accordance with the present invention.

The recesses preferably extend outward into the vertebral bone or into the intervertebral discs so that anchoring surfaces are formed that are generally normal or at an angle to the axis of the anterior or posterior TASIF axial bore(s) 22 or 152 traversing the recesses. The anchoring surfaces accommodate outwardly extending anchor portions or structures of the elongated spinal implants to maintain them in position within the anterior or posterior TASIF axial bore(s) 22 or 152.

Figure 29:
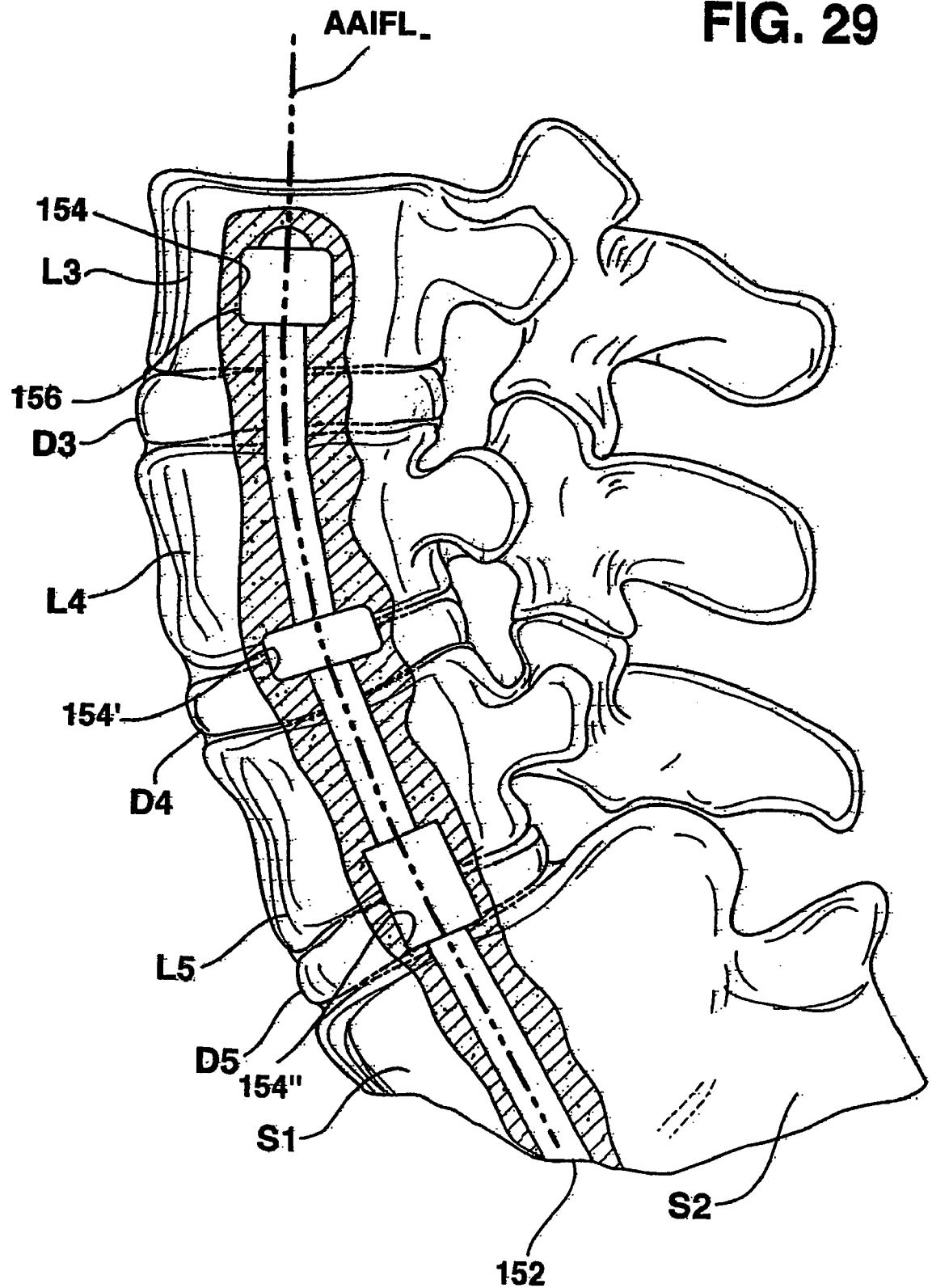
FIG. 29 is a partial cross-section side view of a TASIF axial bore counterbored to form an anchoring recess along the caudal end thereof.

FIG. 29 illustrates an anterior TASIF axial bore 152 extending into vertebral body L3, for example, where a counterbore recess 154 of greater diameter than the diameter of the anterior TASIF axial bore 152 is formed within the cancellous bone. It will be understood that the counterbore recess 154 can be formed having an annular anchoring surface 156 extending outwardly from the anterior TASIF axial bore 152. The depicted counterbore recess 154 is formed in a cylindrical barrel shape, but it will be understood the shape can be more spherical or hemispherical depending upon the tool employed to form it. It is expected that recesses 154 can be formed both at the cephalad end of the TASIF axial bore as depicted in FIG. 29 and in more caudal vertebral bodies.

Moreover, it is anticipated that one or more recess can be formed extending into the intervertebral disc space, e.g. at disc D5 or D4 or D3 depicted in FIG. 29. For example, a disc recess 154' is depicted in disc D4. The disc recess 154' can be wholly within the disc D4, exposing the opposed vertebral body faces of L5 and L4 or extend in to the bone of L5 and/or L4.

A wide variety of tools having bore enlarging cutting heads can be employed to counterbore the recess 154, 154', as long as they can be delivered and operated through the anterior TASIF axial bore(s) or posterior TASIF axial bore(s) 22. It is necessary that the cutting head be delivered to the cephalad end or other site of the axial bore by way of an elongated flexible counterbore drive shaft that can conform to the curvature of the axial bore. The flexible tool drive shaft would be driven, typically rotated, within the confines of the axial bore to cause the cutting tool to counterbore the recess 154, 154' at the selected site. The elongated flexible counterbore drive shaft and distal cutting tool can be delivered directly through the axial bore and guided thereby to the selected location for forming a recess. Or, they can be delivered through a flexible protective outer sheath and/or over a guidewire previously placed and attached to vertebral bone at the cephalad end of the axial bore. Then, the cutting tool is deployed at the selected site, preferably by rotation through the flexible tool drive shaft or through manipulation of a deployment wire or the like, to extend outward of the axial bore. The flexible tool drive shaft is then rotated by a drive motor attached to its proximal end outside the patient's body to rotate the cutting tool to cut or abrade away the cancellous bone or disc body thereby enlarging the bore diameter to counterbore the recess. After the recess is formed, the cutting tool is retracted by manipulation of a deployment wire or automatically when the drive motor is turned off. For simplicity, the following descriptions of preferred counterbore tools describe forming recess 154 within a vertebral body, but apply as well to forming a disc recess 154'.

A First Exemplary Counterbore Tool:

FIGS. 30-32 depict one such motor driven recess forming tool 400 comprising the schematically depicted drive motor 402 coupled to the proximal end of a drive shaft 404 within the lumen 406 of an elongated flexible sheath 410. The drive shaft 404 is formed with a drive shaft lumen 412 enclosing a pull wire 414 that extends proximally from the drive shaft connection with the drive motor 402 through the drive motor 402 to a proximal pull wire manipulator 416 A cutting head 420 having a cutting tool lumen is attached to and extends distally from the drive shaft distal end 418 to a cutting tool distal end 422. The distal end of the pull wire 414 extends from the distal end opening of the drive shaft lumen through the cutting tool lumen and to a fixed connection with the cutting tool distal end 422.

The cutting head 420 is formed of a thin flexible metal tube that is slit lengthwise into a number N cutting tool bands $424_1$ to $424_n$. The N cutting tool bands $424_1$ to $424_n$ are spring-like and normally are straight as depicted in FIG. 30. The recess forming tool 400 is inserted through the posterior or anterior TASIF axial bore 22 or 152 to a selected site, e.g., the cephalad end within the most cephalad lumbar vertebral body, in the configuration depicted in FIG. 30.

Then, pull wire 414 is pulled proximally from proximal manipulator 416 and fixed at a first retracted position to commence counter boring the recess within the soft spongy cancellous bone of the vertebral body. The pull wire 414 pulls the cutting tool distal end 422 proximally causing the N cutting tool bands $424_1$ to $424_n$ to bow outward as shown in FIG. 31. Then the pull wire proximal manipulator 416 is locked in position, e.g., by a chuck mechanism, and the drive motor 402 is energized to rotate the cutting head 420 through mutual rotation of the drive shaft 404 and the pull wire 414. The sharp edges of the cutting tool bands $424_1$ to $424_n$ cut away the surrounding vertebral bone, and the cutting tool bands $424_1$ to $424_n$ expand further outward until the rotation is halted. The pull wire 414 can be pulled back more proximally and set again to expand the cutting tool bands $424_1$ to $424_n$ outward further as shown in FIG. 32 If further enlargement of the recess is desired.

The rotation of the cutting tool bands $424_1$ to $424_n$ is halted when a desired size of the recess is achieved. The pull wire 414 is then released to restore the cutting head 420 to the straight shape depicted in FIG. 30. The cutting tool 400 is either retracted completely from or is retracted to a more caudal location within the posterior or anterior TASIF axial bore 22 or 152 to counterbore a more caudal counterbore recess in the same manner as described above.

The cutting tool 400 can be varied in many respects, e.g., by changing the shape, length, number and materials used for the cutting tool bands $424_1$ to $424_n$. Moreover, it would be possible to employ a push wire to push the cutting tool bands $424_1$ to $424_n$ from the configuration of FIG. 30 to the outwardly expanded configurations of FIGS. 31 and 32.

In addition, the proximal manipulator 416 can be replaced by a material feed length metering tool that automatically pulls the pull wire 414 (or pushes in the case of a push wire) until resistance is met when the drive motor 402 is de-energized to increase the outward expansion of the cutting tool bands $424_1$ to $424_n$.

Figure 33:
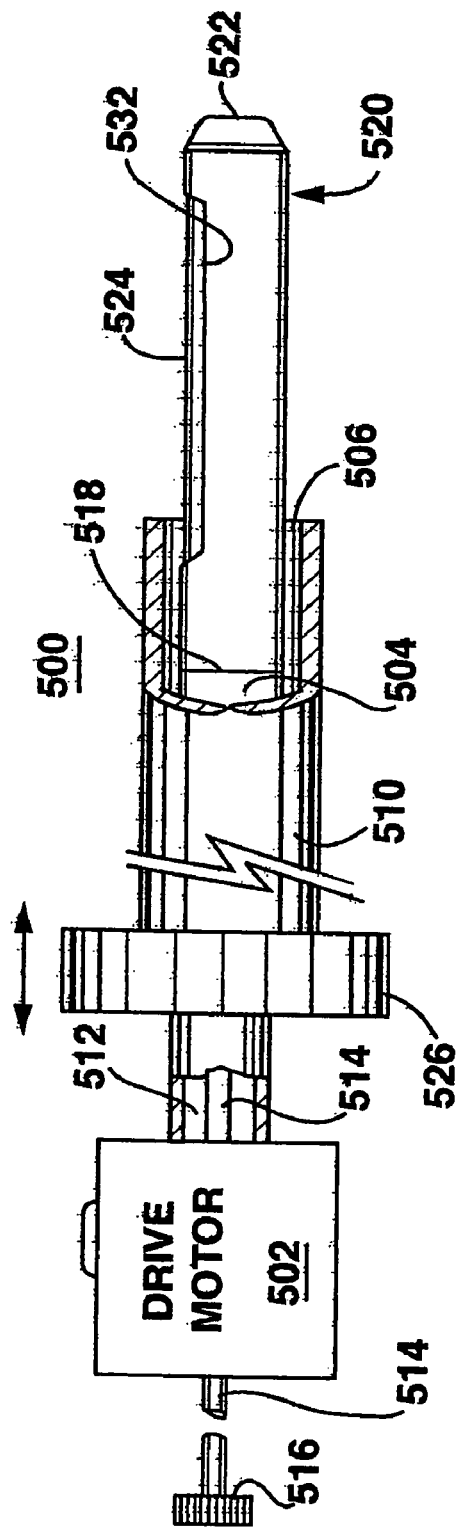
FIGS. 33-34 depict a second exemplary embodiment of a counterbore tool for forming an anchoring recess of the type depicted in FIG. 29.
Figure 34:
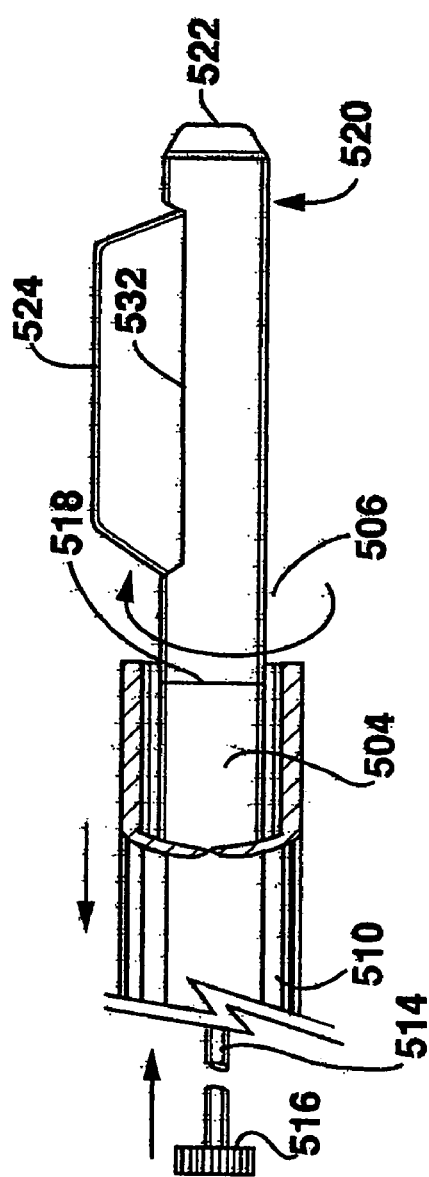

A Second Exemplary Counterbore Tool:

A further cutting tool 500 is depicted in FIGS. 33 and 34, wherein the schematically depicted drive motor 502 is coupled to the proximal end of a drive shaft 504 within the lumen 506 of an elongated flexible sheath 510. The drive shaft 504 is formed with a drive shaft lumen 512 enclosing a push wire 514 that extends proximally from the drive shaft connection with the drive motor 502 through the drive motor 502 to a proximal push wire manipulator 516. A cutting head 520 having a cutting tool lumen is attached to and extends distally from the drive shaft distal end 518 to a cutting tool distal end 522.

The cutting head 520 is formed of a thin flexible metal tube that is slit lengthwise to form a gap 532, and a cutting tool wire or band 524 extends the length of the gap 532. The distal end of the cutting tool wire or band is fixed to the interior of the cutting head 520 at or near the distal end 522. The distal end of the push wire 514 is attached to the proximal end of the cutting tool wire or band 524 within the drive shaft lumen 512. The cutting tool wire or band 524 is spring-like and normally is straight when push wire manipulator 516 is pulled proximally as depicted in FIG. 33. The recess forming tool 500 is inserted through the posterior or anterior TASIF axial bore 22 or 152 to a selected site, e.g., the cephalad end within the most cephalad lumbar vertebral body, in the configuration depicted in FIG. 33.

Then, push wire 514 is pushed distally from proximal manipulator 516 and fixed at an extended position to commence counter boring the recess within the soft spongy cancellous bone of the vertebral body. The push wire 514 pushes the cutting wire or band 524 out of the gap 532 as shown in FIG. 34. The cutting wire or band 524 may be formed of a material, e.g., a superelastic metal alloy, and have a number of pre-formed bends or angles so that it forms a more squared off extended profile as depicted in FIG. 34. Then, the push wire proximal manipulator 516 is locked in position, e.g., by a chuck mechanism, and the drive motor 502 is energized to rotate the cutting head 520 through mutual rotation of the drive shaft 504 and the push wire 514. The sharp edges of the cutting tool wire or band 524 cuts away the surrounding vertebral bone, and the cutting tool wire or band 524 expands further outward until the rotation is halted. The push wire 514 can be pushed more distally and set again to expand the cutting tool band or wire 524 outward further If further enlargement of the recess is desired.

The rotation of the cutting tool or band 524 is halted when a desired size of the recess is achieved. The push wire 514 is then released to restore the cutting head 520 to the straight shape depicted in FIG. 33. The cutting tool 500 is either retracted completely from or is retracted to a more caudal location within the posterior or anterior TASIF axial bore 22 or 152 to counterbore a more caudal counterbore recess in the same manner as described above.

A Third Exemplary Counterbore Tool:

A further cutting tool 600 is depicted in FIGS. 35 and 36, wherein the schematically depicted drive motor 602 is coupled to the proximal end of a drive shaft 604 within the lumen 606 of an elongated, movable, flexible outer sheath 610. A cutting head 620 is attached to and extends distally from the drive shaft distal end 618 to a cutting tool distal end 622.

The cutting head 620 is formed of a one or a plurality N of abrading cables $624_1$-$624_n$ that are attached to or crimped into a lumen of the drive shaft distal end 618 and are of relatively short length. The abrading cables $624_1$-$624_n$ are formed of a woven or braided metal or fabric that are preferably coated or otherwise formed with an abrasive compound and tend to spring outward when unrestrained.

The cutting head 620 is advanced to the site for forming the recess 154 while retracted within the outer sheath lumen 606 as shown in FIG. 35. Then, the outer sheath 610 is retracted by pulling back on the handle or grip 616 and the abrading cables $624_1$-$624_n$ extend outward. The free ends of the abrading cables $624_1$-$624_n$ flail against and abrade away the surrounding vertebral body bone when the drive shaft 612 is rotated by drive motor 602. The drive shaft 612 can be retracted or extended within the TASIF axial bore to form a recess of a desired length.

The abrading cables $624_1$-$624_n$ are depicted as extending distally from the drive shaft distal end 618, so that they tend to spread apart to flail at the surrounding bone when the drive shaft 612 is rotated by drive motor 602. However, it will be understood that the abrading cables $624_1$-$624_n$ can be attached to the drive shaft 612 to extend at right angles to the drive shaft 612 such that they are wound about it when retracted within lumen 606. Then when the abrading cables $624_1$-$624_n$ are released, they tend to extend outward laterally to the axis of the drive shaft 612 when it is rotated.

A Fourth Exemplary Counterbore Tool:

More rigid boring or cutting elements can be employed than flexible cables including knives, routing bits and saw teeth that are retracted when passed through the TASIF axial bore and then either passively or actively extended outward to bore out a recess in the axial bore wall. FIGS. 37-40 depict an exemplary embodiment of a counterbore tool 700 for forming an anchoring recess of the type depicted in FIG. 29. The cutting head 720 comprises a pair of cutting blades $724_1$ and $724_2$ that are located in a cross-bore 740 as shown in FIG. 40 and are retracted during introduction as shown in FIG. 37 and extended in use as shown in FIGS. 38-40.

The schematically depicted drive motor 702 is coupled to the proximal end of a drive shaft 704 that is enclosed within the lumen 706 of an elongated flexible sheath 710 that is movable from an advanced position of FIG. 37 to a retracted position of FIGS. 38-40. The drive shaft 704 is formed with a drive shaft lumen 712 extending from the drive motor 702 to the junction 718 with the cutting head 720 that extends to the drive shaft distal end 722. The drive shaft lumen 712 encloses a twist wire 714 that extends proximally from the drive shaft connection with the drive motor 702 through the drive motor 702 to a proximal twist wire manipulator 716. The distal end of the twist wire 714 is forked to form pins 742 and 744 that are extended through bores 746 and 748, respectively, of cutting blades $724_1$ and $724_2$, respectively.

The cutting blades $724_1$ and $724_2$ are normally located within the bore 740 as the recess forming tool 400 is inserted through the posterior or anterior TASIF axial bore 22 or 152 to a selected site, e.g., the cephalad end within the most cephalad lumbar vertebral body, in the configuration depicted in FIG. 37. The outer sheath 710 may or may not be employed, but extends over the retracted cutting blades $724_1$ and $724_2$ as depicted in FIG. 37.

Then, twist wire 714 is twisted from proximal manipulator 716 and fixed at an extended position to commence counter boring the recess within the soft spongy cancellous bone of the vertebral body. The sharp edges of the cutting blades $724_1$ and $724_2$ cut away the surrounding vertebral bone. The twist wire 714 can be twisted further so that the cutting blades $724_1$ and $724_2$ extend further outward as the boring progresses If further enlargement of the recess is desired. An automatic twist mechanism can be substituted for the proximal manipulator 716 to cause it to automatically twist the twist wire 714 as the recess is enlarged.

The rotation of the cutting head 720 is halted when a desired size of the recess is achieved. The twist wire 714 is then twisted in the opposite direction to retract the cutting blades $724_1$ and $724_2$ to the retracted position of FIG. 37. The cutting head 720 is either withdrawn completely from or is retracted to a more caudal location within the posterior or anterior TASIF axial bore 22 or 152 to counterbore a more caudal counterbore recess in the same manner as described above.

There are other possible ways of restraining and extending the cutting blades $724_1$ and $724_2$ within and from the bore 740. In one alternative embodiment, the cutting blades $724_1$ and $724_2$ can be loosely restrained or hinged within the bore 740 such that centrifugal force causes the cutting blades $724_1$ and $724_2$ to extend outward as the drive shaft 704 is rotated by motor 702 and the soft cancellous bone of the vertebral body is cut away. In a further approach, the centrifugal force can be augmented by trapped springs within the bore 740.

A Fifth Exemplary Counterbore Tool:

FIGS. 41 and 42 depict an exemplary embodiment of a counterbore tool 800 for forming an anchoring recess of the type depicted in FIG. 29. The cutting head 820 comprises an elongated spade bit or blade 824 that is pivotal from an in-line retracted configuration depicted in FIG. 41 during introduction and withdrawal and an deployed extended position depicted in FIG. 42. The elongated blade 824 is pivotally attached to the drive shaft distal end 818 and to the distal end of push wire 814 to move a cutting edge 832 into contact and away from with cancellous bone. One of several possible shapes for the cutting edge 832 of the cutting blade 824 is depicted in FIGS. 41 and 42.

The schematically depicted drive motor 802 is coupled to the proximal end of a drive shaft 804 that is enclosed within the lumen 806 of an elongated flexible sheath 810 that is movable from an advanced position of FIG. 41 to a retracted position of FIG. 42. The outer sheath 810 extends between a proximal sheath manipulator 826 and a distal sheath end 836.

The drive shaft 804 is formed with a drive shaft lumen 812 extending from the drive motor 802 to the junction 818 with the cutting head 820 that extends to the drive shaft distal end 822. The drive shaft lumen 812 encloses a tip deflection wire 814 that extends proximally from the drive shaft connection with the drive motor 802 through the drive motor 802 to a proximal tip deflection wire manipulator 816. The distal end of the tip deflection wire 814 is attached to proximal extension 834 of blade 824 via a rotatable connection.

A pin and slot hinge 830 is formed between the blade 824 and in the drive shaft end 822. A flange having an elongated slot is formed inside the drive shaft lumen 812, and a hole is formed through the blade 824. The proximal end of a hinge pin is trapped within the elongated slot, and the distal end of the hinge pin is trapped within the circular hole formed through the blade 824. There are many possible equivalent ways of hinging and extending the cutting blade 824 to angle the cutting edge 832 to the cancellous bone.

In use, the cutting tool 820 is introduced to the site within the TASIF axial bore 22 or 152 where the recess is to be formed with the cutting blade 824 in the retracted position of FIG. 41. When the tip deflection wire 814 is pushed, the proximal end of the hinge pin slides along the slot toward its distal end, and the distal end of the hinge pin rotates within the circular hole, thereby pivoting the cutting blade 824 from the retracted position of FIG. 41 to the extended position of FIG. 42. Then, the drive motor 802 is energized to rotate the drive shaft 804 and the extended cutting blade 824. Again, pushing force can be applied manually or automatically on the tip deflection wire manipulator 816 as the cutting blade 824 is rotated and cuts away the cancellous bone to thereby incrementally extend the cutting blade from the retracted position of FIG. 41 to the fully extended position of FIG. 42. The cutting tool 820 can be moved distally or proximally to lengthen and shape the recess that is formed.

The rotation of the cutting head 820 is halted when a desired size and shape of the recess is achieved. The tip deflection wire 814 is pulled proximally, causing the proximal end of the hinge pin to slide along the slot to its proximal end and the distal end of the hinge pin to rotate within the circular hole. The cutting blade 824 then pivots from the extended position of FIG. 42 to the retracted position of FIG. 41. The recess forming tool 800 can then be retracted. The cutting head 820 is either withdrawn completely from or is retracted to a more caudal location within the posterior or anterior TASIF axial bore 22 or 152 to counterbore a more caudal counterbore recess in the same manner as described above.

SUMMARY

It will be understood that features of the above described cutting heads can be substituted for one another or combined together. For example, abrading materials or abrasive coated surfaces may substituted for sharpened cutting blade edges or added to such edges or to cutting wire surfaces.

The curved, posterior and anterior TASIF axial bores 22 and 152 that are formed in step S200 of FIG. 6 as described above start in the sacrum at the respective posterior and anterior target points and extend upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. An inspection of the vertebral bodies and discs along the sides of the posterior or anterior TASIF axial bore 22 or 152 can be made using an elongated endoscope inserted therethrough (or through a pilot hole if one is formed earlier). A discectomy or disc augmentation and/or vertebroblasty may be performed pursuant to step S300 of FIG. 6 through the posterior or anterior TASIF axial bore 22 or 152 to relieve the patient's symptoms and aid in the fusion achieved by insertion of a spinal implant. In such procedures, materials or devices can be inserted through the curved, posterior and anterior TASIF axial bores 22 and 152 to fit into excised disc space or damaged vertebral bodies.

It will be understood that various types of axial spinal implants can be inserted into the above-described curved, posterior and anterior TASIF axial bores 22 and 152. When a counterbore recess is formed as described above, it receives anchor members of the axial spinal implant to maintain it in place. Such axial spinal implants can be combined with laterally installed disc replacements or spacers.

The preferred embodiments of the present invention for forming recesses within axial bores have been described above in relation specifically to curved axial bores. However, it will be understood that the methods and apparatus for forming such recesses can advantageously be practiced within straight or relatively straight axial bores. Moreover, it will be understood that such recesses may be formed at the caudal end of the axial bores or at one or more location intermediate the cephalad and caudal ends of straight, curved, and diverging axial bores.

What is claimed is:

1. Apparatus for providing access to a series of adjacent vertebrae located within a human lumbar and sacral spine having an anterior aspect, a posterior aspect and an axial aspect from an anterior or posterior sacral target point of a sacral vertebra in alignment with a visualized, axial instrumentation/fusion line extending in the axial aspect through the series of adjacent vertebral bodies, wherein the axial aspect is curved in the posterior-anterior plane due to curvature of the spinal column, the vertebrae separated by intact or damaged spinal discs, the apparatus comprising:
   a controllable boring device configured for boring a curved trans-sacral axial bore from the accessed sacral target point in alignment with the axial instrumentation/fusion line cephalad and axially through the vertebral bodies of the series of adjacent vertebrae and any intervertebral spinal discs; and
   a bore enlarging tool sized to fit within the curved axial bore, the tool adapted to be inserted from the accessed sacral target point to a selected location along the curved axial bore, the tool operable to enlarge a section of the curved axial bore to form at least one recess therein;
   wherein the controllable boring device comprises an elongated drill shaft assembly comprising:
   a drill bit attached to a flexible drive shaft;
   a sheath with an inner lumen for receiving the flexible drive shaft, the sheath comprising a distal segment and one or more radially offset tip deflection wire lumens; and
   one or more tip deflection wires disposed in the one or more radially offset tip deflection wire lumens for imparting a desired curvature in the distal segment of the sheath;
   wherein the bore enlarging tool comprises a counterboring tool assembly comprising:
   an elongate drive shaft extending between a shaft proximal end and a shaft distal end, the shaft having a shaft lumen;
   a cutting head mounted to the shaft distal end, the cutting head comprising deployment/retraction means for deploying the cutting head from a retracted locked position to a deployed locked position and for retracting the cutting head from the deployed locked position to the retracted locked position, the cuffing head capable of cuffing away bone or intervertebral disc material while in the deployed locked position; and
   rotating means for rotating the cutting head from the shaft distal end to cut away vertebral bone or disc material.

2. The apparatus of claim 1, wherein the retracted locked position comprises a radially retracted locked position.

3. The apparatus of claim 1, wherein the retracted locked position comprises an axially retracted locked position.

4. The apparatus of claim 1, wherein the deployed locked position comprises a radially deployed locked position.

5. The apparatus of claim 1, wherein the deployed locked position comprises an axially deployed locked position.

6. The apparatus of claim 1, wherein the rotating means comprises a cutting head motor attached to the shaft proximal end.

7. The apparatus of claim 1, wherein the cutting head further comprises:
   a thin, flexible, tubular member extending distally from a cutting head proximal end located at the shaft distal end to a cutting head distal end; and
   an elongated cutting wire extending between a cutting wire proximal end and a cutting wire distal end, the cutting wire proximal and distal ends extending into the flexible tubular member.

8. The apparatus of claim 1, wherein the cutting head further comprises at least one abrading cable attached to the shaft distal end.

9. The apparatus of claim 8, wherein the at least one cable is formed of a length of woven or braided metal or fabric tending to spring outward when unrestrained.

10. The apparatus of claim 8, wherein the bore counterboring tool assembly further comprises an elongated, flexible, restraining sheath having a sheath lumen extending from a sheath proximal end to a sheath distal end through which the drive shaft extends and within which the at least one abrading cable is enclosed in a restrained configuration during passage through the curved axial bore.

11. Apparatus for providing access to a series of adjacent vertebrae located within a human lumbar and sacral spine having an anterior aspect, a posterior aspect and an axial aspect from an anterior or posterior sacral target point of a sacral vertebra in alignment with a visualized, axial instrumentation/fusion line extending in the axial aspect through the series of adjacent vertebral bodies, wherein the axial aspect is curved in the posterior-anterior plane due to curvature of the spinal column, the vertebrae separated by intact or damaged spinal discs, the apparatus comprising:
   a controllable boring device configured for boring a curved, trans-sacral axial bore from the accessed sacral target point in alignment with the axial instrumentation/fusion line cephalad and axially through the vertebral bodies of the series of adjacent vertebrae and any intervertebral spinal discs; and
   a bore enlarging tool sized to fit within the curved axial bore, the tool adapted to be inserted from the accessed sacral target point to a selected location along the curved axial bore, the tool operable to enlarge a section of the curved axial bore to form at least one recess therein;
   wherein the controllable boring device comprises an elongated drill shaft assembly comprising:
   a flexible drive shaft;
   an exposed drill bit attached to a distal end of the flexible drive shaft; and
   a pre-curved inner sheath, and an outer sheath configured to move over the pre-curved inner sheath;
   wherein the bore enlarging tool comprises a counterboring tool assembly comprising:
   an elongate drive shaft extending between a shaft proximal end and a shaft distal end, the shaft having a shaft lumen;
   a cutting head mounted to the shaft distal end, the cutting head comprising deployment/retraction means for deploying the cutting head from a retracted locked position to a deployed locked position and for retracting the cutting head from the deployed locked position to the retracted locked position, the cutting head capable of cuffing away bone or intervertebral disc material while in the deployed locked position; and
   rotating means for rotating the cutting head from the shaft distal end to cut away vertebral bone or disc material.

12. The apparatus of claim 11, wherein the retracted locked position comprises a radially retracted locked position.

13. The apparatus of claim 11, wherein the retracted locked position comprises an axially retracted locked position.

14. The apparatus of claim 11, wherein the deployed locked position comprises a radially deployed locked position.

15. The apparatus of claim 11, wherein the deployed locked position comprises an axially deployed locked position.

16. The apparatus of claim 11, wherein the rotating means comprises a cutting head motor attached to the shaft proximal end.

17. Apparatus for providing access to a series of adjacent vertebrae located within a human lumbar and sacral spine having an anterior aspect, a posterior aspect and an axial aspect from an anterior or posterior sacral target point of a sacral vertebra in alignment with a visualized, axial instrumentation/fusion line extending in the axial aspect through the series of adjacent vertebral bodies, wherein the axial aspect is curved in the posterior-anterior plane due to curvature of the spinal column, the vertebrae separated by intact or damaged spinal discs, the apparatus comprising:
- a controllable boring device configured for boring a curved, trans-sacral axial bore from the accessed sacral target point in alignment with the axial instrumentation/fusion line cephalad and axially though the vertebral bodies of the series of adjacent vertebrae and any intervertebral spinal discs; and
- a bore enlarging tool sized to fit within the curved axial bore, the tool adapted to be inserted from the accessed sacral target point to a selected location along the curved axial bore, the tool operable to enlarge a section of the curved axial bore to form at least one recess therein;

wherein the controllable boring device comprises:
a flexible drive shaft;
a drill bit attached to a distal end of the flexible drive shaft;
a sheath with an inner lumen for receiving the flexible drive shaft, the sheath comprising a distal segment and one or more radially offset tip deflection wire lumens; and
one or more tip deflection wires disposed in the one or more radially offset tip deflection wire lumens for imparting a desired curvature in the distal segment of the sheath.

18. Apparatus for providing access to a series of adjacent vertebrae located within a human lumbar and sacral spine having an anterior aspect, a posterior aspect and an axial aspect from an anterior or posterior sacral target point of a sacral vertebra in alignment with a visualized, axial instrumentation/fusion line extending in the axial aspect though the series of adjacent vertebral bodies, wherein the axial aspect is curved in the posterior-anterior plane due to curvature of the spinal column, the vertebrae separated by intact or damaged spinal discs, the apparatus comprising:
- a controllable boring device configured for boring a curved, trans-sacral axial bore from the accessed sacral target point in alignment with the axial instrumentation/fusion line cephalad and axially though the vertebral bodies of the series of adjacent vertebrae and any intervertebral spinal discs; and
- a bore enlarging tool sized to fit within the curved axial bore, the tool adapted to be inserted from the accessed sacral target point to a selected location along the curved axial bore, the tool operable to enlarge a section of the curved axial bore to form at least one recess therein;

wherein the controllable boring device comprises:
a flexible drive shaft;
a drill bit attached to a distal end of the flexible drive shaft;
a pre-curved sheath with an inner lumen for receiving the flexible drive shaft and an outer sheath configured to move over the pre-curved sheath.

19. Apparatus for providing access to a series of adjacent vertebrae located within a human lumbar and sacral spine having an anterior aspect, a posterior aspect and an axial aspect from an anterior or posterior sacral target point of a sacral vertebra in alignment with a visualized, axial instrumentation/fusion line extending in the axial aspect through the series of adjacent vertebral bodies, wherein the axial aspect is curved in the posterior-anterior plane due to curvature of the spinal column, the vertebrae separated by intact or damaged spinal discs, the apparatus comprising:
- a controllable boring device configured for boring a curved, trans-sacral axial bore from the accessed sacral target point in alignment with the axial instrumentation/fusion line cephalad and axially through the vertebral bodies of the series of adjacent vertebrae and any intervertebral spinal discs; and
- a bore enlarging tool sized to fit within the curved axial bore, the tool adapted to be inserted from the accessed sacral target point to a selected location along the curved axial bore, the tool operable to enlarge a section of the curved axial bore to form at least one recess therein;

wherein the controllable boring device comprises:
a flexible drive shaft;
a drill bit attached to a distal end of the flexible drive shaft; and
a sheath with an inner lumen for receiving the flexible drive shaft, wherein the sheath comprises a sheath longitudinal axis, the inner lumen being radially offset from the sheath longitudinal axis to locate the drill bit offset from the sheath longitudinal axis.

\* \* \* \* \*

UNITED STATES PATENT AND TRADEMARK OFFICE
CERTIFICATE OF CORRECTION

PATENT NO. : 7,569,056 B2
APPLICATION NO. : 10/853476
DATED : August 4, 2009
INVENTOR(S) : Andrew H. Cragg and Jonathan Kagan It is certified that error appears in the above-identified patent and that said Letters Patent is hereby corrected as shown below:

At column 1, page 4 (Other Publications), item 56, line 33, delete ""Arthoscopic" and insert --"Arthroscopic--.

At column 1, page 4 (Other Publications), item 56, line 43, delete "lumber" and insert --lumbar--.

At column 2, page 4 (Other Publications), item 56, line 8, delete ""Arthoscopic" and insert --"Arthroscopic--.

At column 2, page 4 (Other Publications), item 56, line 18, delete ""Arthoscopic" and insert --"Arthroscopic--.

At column 2, page 4 (Other Publications), item 56, line 21, after "Appl." insert --Pub.--.

At column 2, page 4 (Other Publications), item 56, line 23, after "Appl." insert --Pub.--.

At column 2, page 4 (Other Publications), item 56, line 42, delete "Euoprean" and insert --European--.

At column 1, line 31, delete "VERTEBRAE" and insert --VERTEBRAE,--.

At column 2, line 59, delete "sophisticated" and insert --sophisticated.--.

At column 2, line 60, delete "diagnostic" and insert --Diagnostic--.

At column 4, line 36-37, delete "anterior lateral" and insert --anterolateral--.

At column 4, line 48, delete "anterior lateral" and insert --anterolateral--.

At column 9, line 57, delete "vertebroblasty" and insert --vertebroplasty--.

At column 11, line 5, delete "periostium" and insert --periosteum--.

At column 14, line 10, after "of the" delete "of the". (Second Occurence)

At column 16, line 26, delete "guide wire" and insert --guidewire--.

At column 17, line 12, after "in" delete "a".

At column 19, line 44, delete "If" and insert --if--.

At column 20, line 66, delete "If" and insert --if--.

CERTIFICATE OF CORRECTION (continued)
U.S. Pat. No. 7,569,056 B2

At column 21, line 29, delete "an" and insert --a--.

At column 22, line 46, delete "vertebroblasty" and insert --vertebroplasty--.

At column 23, line 46, in claim 1, delete "cuffing" and insert --cutting--.

At column 23, line 47, in claim 1, delete "cuffing" and insert --cutting--.

At column 24, line 56, in claim 11, delete "cuffing" and insert --cutting--.

At column 25, line 20, in claim 17, delete "though" and insert --through--.

At column 25, line 42, in claim 18, delete "though" and insert --through--.

At column 26, line 2, in claim 18, delete "though" and insert --through--.

At column 26, line 14, in claim 18, delete "shaft" and insert --shaft;--.

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,569,056 B2
APPLICATION NO. : 10/853476
DATED : August 4, 2009
INVENTOR(S) : Cragg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Seventh Day of September, 2010

David J. Kappos
*Director of the United States Patent and Trademark Office*